US010126659B2

(12) United States Patent
Zijp et al.

(10) Patent No.: US 10,126,659 B2
(45) Date of Patent: Nov. 13, 2018

(54) METHOD AND APPARATUS FOR INSPECTION AND METROLOGY

(71) Applicant: ASML NETHERLANDS B.V., Veldhoven (NL)

(72) Inventors: Ferry Zijp, Nuenen (NL); Sietse Thijmen Van Der Post, Utrecht (NL); Fanhe Kong, Eindhoven (NL); Duygu Akbulut, Eindhoven (NL)

(73) Assignee: ASML NETHERLANDS B.V., Veldhoven (NL)

( * ) Notice: Subject to any disclaimer, the term of this patent is extended or adjusted under 35 U.S.C. 154(b) by 72 days.

(21) Appl. No.: 15/286,319

(22) Filed: Oct. 5, 2016

(65) Prior Publication Data

US 2017/0102620 A1    Apr. 13, 2017

(30) Foreign Application Priority Data

Oct. 9, 2015  (EP) .................... 15189237

(51) Int. Cl.
*G03B 27/68* (2006.01)
*G03F 7/20* (2006.01)
(Continued)

(52) U.S. Cl.
CPC ....... *G03F 7/70133* (2013.01); *G02B 21/242* (2013.01); *G03F 7/70625* (2013.01); *G03F 7/70633* (2013.01); *G01N 21/956* (2013.01)

(58) Field of Classification Search
CPC ............ G03F 7/70133; G03F 7/70625; G03F 7/70633; G01N 21/956; G02B 21/242
See application file for complete search history.

(56) References Cited

U.S. PATENT DOCUMENTS 5,208,648 A    5/1993  Batchelder et al.
6,476,382 B1 *  11/2002  Zhai .................... G03F 7/70383
                                                250/237 G
(Continued)

FOREIGN PATENT DOCUMENTS

EP    2 003 681    12/2008
EP    2 048 543     4/2009
(Continued)

OTHER PUBLICATIONS

International Search Report and Written Opinion dated Jan. 2, 2017 in corresponding International Patent Application No. PCT/EP2016/072412.
(Continued)

*Primary Examiner* — Deoram Persaud
(74) *Attorney, Agent, or Firm* — Pillsbury Winthrop Shaw Pittman LLP

(57) ABSTRACT

A method including obtaining a plurality of radiation distributions of measurement radiation redirected by the target, each of the plurality of radiation distributions obtained at a different gap distance between the target and an optical element of a measurement apparatus, the optical element being the nearest optical element to the target used to provide the measurement radiation to the target, and determining a parameter related to the target using data of the plurality of radiation distributions in conjunction with a mathematical model describing the measurement target.

20 Claims, 9 Drawing Sheets

(51) Int. Cl.
*G02B 21/24* (2006.01)
*G01N 21/956* (2006.01)

(56) References Cited

U.S. PATENT DOCUMENTS

| | | | |
|---|---|---|---|
| 7,330,279 | B2 | 2/2008 | Vuong et al. |
| 7,580,131 | B2 | 8/2009 | Den Boef |
| 7,791,732 | B2 | 9/2010 | Den Boef et al. |
| 7,852,459 | B2 | 12/2010 | Den Boef et al. |
| 8,125,615 | B2 | 2/2012 | Kalf et al. |
| 8,411,287 | B2 | 4/2013 | Smilde et al. |
| 9,081,303 | B2 | 7/2015 | Cramer et al. |
| 9,261,772 | B2 | 2/2016 | Quintanilha |
| 9,851,246 | B2* | 12/2017 | Van Der Post ........... G01J 1/44 |
| 2006/0066855 | A1 | 3/2006 | Den Boef et al. |
| 2007/0046953 | A1* | 3/2007 | De Groot ........... G01B 11/0675 |
| | | | 356/512 |
| 2007/0217300 | A1 | 9/2007 | Koyama et al. |
| 2007/0297301 | A1* | 12/2007 | Verschuren .......... G11B 7/0956 |
| | | | 369/44.32 |
| 2008/0186482 | A1 | 8/2008 | Den Boef et al. |
| 2008/0259343 | A1 | 10/2008 | Den Boef |
| 2008/0279070 | A1 | 11/2008 | Zijp et al. |
| 2009/0040906 | A1* | 2/2009 | Hong ................... G11B 7/0908 |
| | | | 369/112.23 |
| 2009/0091726 | A1 | 4/2009 | Kalf et al. |
| 2009/0190461 | A1* | 7/2009 | Van Der Mark .... G11B 7/1374 |
| | | | 369/112.23 |
| 2009/0219790 | A1* | 9/2009 | Zijp ................. G11B 11/10536 |
| | | | 369/13.32 |
| 2010/0232264 | A1* | 9/2010 | Narumi ................ G11B 7/0908 |
| | | | 369/44.14 |
| 2011/0002208 | A1* | 1/2011 | Futakuchi ............ G11B 7/0956 |
| | | | 369/53.19 |
| 2011/0027704 | A1 | 2/2011 | Cramer et al. |
| 2011/0043791 | A1 | 2/2011 | Smilde et al. |
| 2011/0273687 | A1* | 11/2011 | Leenders ............... G03B 27/42 |
| | | | 355/53 |
| 2012/0044470 | A1 | 2/2012 | Smilde et al. |
| 2013/0003515 | A1* | 1/2013 | Knappmann ........ G11B 7/0948 |
| | | | 369/112.03 |
| 2013/0271740 | A1 | 10/2013 | Quintanilha |
| 2013/0342831 | A1* | 12/2013 | Levinski ............ G03F 7/70633 |
| | | | 356/237.1 |
| 2014/0019097 | A1 | 1/2014 | Bakeman et al. |
| 2015/0308966 | A1 | 10/2015 | Grootjans et al. |
| 2015/0377795 | A1* | 12/2015 | Zhao ....................... G01N 21/33 |
| | | | 250/372 |
| 2016/0061590 | A1* | 3/2016 | Pandey .................. G01B 11/14 |
| | | | 356/614 |
| 2016/0246189 | A1* | 8/2016 | Van Berkel ........ G03F 7/70775 |
| 2016/0258810 | A1* | 9/2016 | Van Der Post .......... G01J 1/44 |
| 2016/0266503 | A1* | 9/2016 | Van Voorst ............ G01B 11/00 |
| 2017/0315055 | A1* | 11/2017 | Tinnemans ........... G01N 21/47 |
| 2018/0004095 | A1* | 1/2018 | Tukker ................ G03F 7/70191 |

FOREIGN PATENT DOCUMENTS

| | | |
|---|---|---|
| JP | 2008-065931 | 3/2008 |
| TW | 200846839 | 12/2008 |
| TW | 200925796 | 6/2009 |
| WO | 2014/082813 | 6/2014 |

OTHER PUBLICATIONS

Wan-Chin Kim et al., "Effects of optical variables in immersion lens-based near-field optics," Optics Express, vol. 16, No. 18, pp. 13933-13948 (Sep. 1, 2008).

Ravikiran Attota et al., "Optical Through-Focus Technique that Differentiates Small Changes in Line Width, Line Height and Sidewall Angle for CD, Overlay, and Defect Metrology Applications," Proc. of SPIE, vol. 6922, 12 pages (Feb. 24-29, 2008).

Taiwan Office Action dated Sep. 29, 2017 in corresponding Taiwan Patent Application No. 105132654.

\* cited by examiner

METHOD AND APPARATUS FOR INSPECTION AND METROLOGY

This application claims priority and benefit under 35 U.S.C. § 119(a) to European Patent Application No. 15189237.9, filed on Oct. 9, 2015. The content of the foregoing application is incorporated herein in its entirety by reference.

FIELD

The present description relates to a method and apparatus for determining a parameter of interest from a measured radiation distribution captured from a metrology target.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate:

In order to monitor one or more steps of the lithographic process (i.e., a process of device manufacturing involving lithography, including, e.g., resist-processing, etching, development, baking, etc.), the patterned substrate is inspected and one or more parameters of the patterned substrate are measured. The one or more parameters may include, for example, the overlay error between successive layers formed in or on the patterned substrate and/or critical dimension (e.g., linewidth) of developed photosensitive resist and/or etched and deposited structures. This measurement may be performed on a target of the product substrate itself and/or on a dedicated metrology target provided on the substrate. There are various techniques for making measurements of the microscopic structures formed in lithographic processes, including the use of a scanning electron microscope and/or various specialized tools.

A fast and non-invasive form of specialized inspection tool is a scatterometer in which a beam of radiation is directed onto a target on a substrate and properties of the scattered and/or reflected (or more generally redirected) beam are measured. By comparing one or more properties of the beam before and after it has been redirected from the substrate, one or more properties of the substrate (e.g., of one or more of its layers and one or more structure formed in the one or more layers) can be determined. Two main types of scatterometer are known. A spectroscopic scatterometer directs a broadband radiation beam onto the substrate and measures the spectrum (intensity as a function of wavelength) of the radiation redirected into a particular narrow angular range. An angularly resolved scatterometer uses a monochromatic radiation beam and measures the intensity of the redirected radiation as a function of angle.

A particular application of scatterometry is in the measurement of feature asymmetry within a periodic target. This can be used as a measure of overlay error, for example, but other applications are also known. In an angle resolved scatterometer, asymmetry can be measured by comparing opposite parts of the diffraction spectrum (for example, comparing the $-1$st and $+1^{st}$ orders in the diffraction spectrum of a periodic grating). This can be done simply in angle-resolved scatterometry, as is described for example in U.S. patent application publication US2006-066855.

SUMMARY

With reduction of the physical dimensions in lithographic processing, there is demand to, for example, increase measurement accuracy/precision and/or reduce the space occupied by targets dedicated to metrology. Image based scatterometry measurements have been devised to allow the use of smaller targets, by taking separate images of the target using $-1^{st}$ and $+1^{st}$ order radiation in turn. Examples of this image based technique are described in published U.S. patent application publication nos. US2011-0027704, US2011-0043791 and US2012-0044470, which are incorporated herein in their entirety by reference.

Demand for further reduction in target size and for improved accuracy/precision continues, however, and existing techniques suffer from various constraints that make it difficult to maintain accuracy/precision and/or reduce the size of the targets. Another way to improve on inspection and measurement techniques is to use a solid immersion lens (SIL) as the optical element nearest the target surface (e.g., a substrate). The extreme proximity of the SIL with the target surface (e.g., substrate) results in a very high effective numerical aperture (NA) larger than 1. Using an incoherent or coherent radiation source with this SIL allows a very small target to be inspected.

To take advantage of the increasing numerical aperture, the gap between the SIL and the target surface should be set to a desired value. For example, the gap may be within the range of $\lambda/40$ to $\lambda/8$ (where $\lambda$ is the wavelength of the measurement radiation) e.g., within the range of 10-100 nm or 10-50 nm, to have the SIL in effective optical contact with the target surface. An example optical gap measuring method and apparatus can involve detecting cross components of polarization in the high numerical aperture element. The cross polarized signal is then recorded by a detector and can be used as an input parameter into a gap control process. In another example, the gap may be controlled by reference to reflected laser radiation intensity. As will be appreciated, other methods and apparatus may be used to arrive at a signal representative of the gap (e.g., representative of its size or of its variation from a nominal size).

Irrespective of detecting method, the gap between the SIL (or other component) and the target (or other surface) should be established, and maintained at, a desired gap distance or distance range, typically by an associated actuator and control system. This is because the measurement data (e.g., intensity data, image, etc.) derived from the radiation redirected by the target, and obtained using the SIL (or other optical coupling component), depends on the gap, and any parameter of interest (e.g., height of a part of the target pattern, width of a part of the target pattern, thickness of one or more various layers of the target pattern, etc.) as well as the gap distance itself can be reconstructed from the measured data assuming an essentially constant gap distance during data acquisition.

In an embodiment, there is provided a method comprising: obtaining a plurality of radiation distributions of measurement radiation redirected by the target, each of the plurality of radiation distributions obtained at a different gap distance between the target and an optical element of a measurement apparatus, the optical element being the nearest optical element to the target used to provide the measurement radiation to the target; and determining a parameter related to the target using data of the plurality of radiation distributions in conjunction with a mathematical model describing the measurement target.

In an embodiment, at least two of the radiation distributions are obtained with a different respective measurement beam wavelength. In an embodiment, at least two of the radiation distributions are obtained with a different respective measurement beam polarization. In an embodiment, the plurality of radiation distributions is obtained at least in part during a relative motion between the target and the optical element. In an embodiment, the optical element comprises a solid immersion lens. In an embodiment, the radiation distributions are angular resolved detected radiation distributions. In an embodiment, the parameter comprises at least one selected from: a critical dimension of a feature of the target, a radiation focus used to print the target, a radiation dose used to print the target, overlay, and/or alignment. In an embodiment, obtaining the plurality of radiation distributions comprises: illuminating, using the optical element, the target with radiation; and measuring radiation redirected by the target using a detector. In an embodiment, the target comprises a fiducial and the parameter comprises a parameter of an effective medium approximation in the model for roughness of a surface of the optical element. In an embodiment, determining the parameter comprises a target reconstruction. In an embodiment, determining the parameter comprises minimizing a difference between data of the radiation distributions and data of corresponding radiation distributions at the respective different gap distances determined using the model. In an embodiment, the mathematical model comprises a unit cell model representing a period of a periodic structure of the target. In an embodiment, the method comprises a separate unit cell model for each radiation distribution, each unit cell having an identical set of floating parameters of the target and a floating gap distance parameter that is different for each of the unit cells. In an embodiment, the measurement apparatus has numerical aperture of greater than 1. In an embodiment, the optical element is a transparent optical element positioned between the target and an objective having a numerical aperture of less than or equal to 1. In an embodiment, the optical element comprises a partially transparent and partially reflective coating.

In an embodiment, there is provided a method of manufacturing devices wherein a device pattern is applied to a series of substrates using a lithographic process, the method including inspecting at least a target formed as part of or beside the device pattern on at least one of the substrates, using the method of a claim herein, and controlling the lithographic process for later substrates in accordance with the parameter of the method.

In an embodiment, there is provided a non-transitory computer program product comprising machine-readable instructions for causing a processor to cause performance of a method herein.

In an embodiment, there is provided a system comprising: an inspection apparatus configured to provide a beam on a measurement target on a substrate and to detect radiation redirected by the target to determine a parameter of a lithographic process; and a non-transitory computer program product as described herein. In an embodiment, the system further comprises a lithographic apparatus, the lithographic apparatus comprising a support structure configured to hold a patterning device to modulate a radiation beam and a projection optical system arranged to project the modulated onto a radiation-sensitive substrate.

BRIEF DESCRIPTION OF THE DRAWINGS

Embodiments will now be described, by way of example only, with reference to the accompanying drawings in which.

Like reference numerals refer to like components throughout the figures.

DETAILED DESCRIPTION

Before describing embodiments in detail, it is instructive to present an example environment in which embodiments may be implemented.

Figure 1:
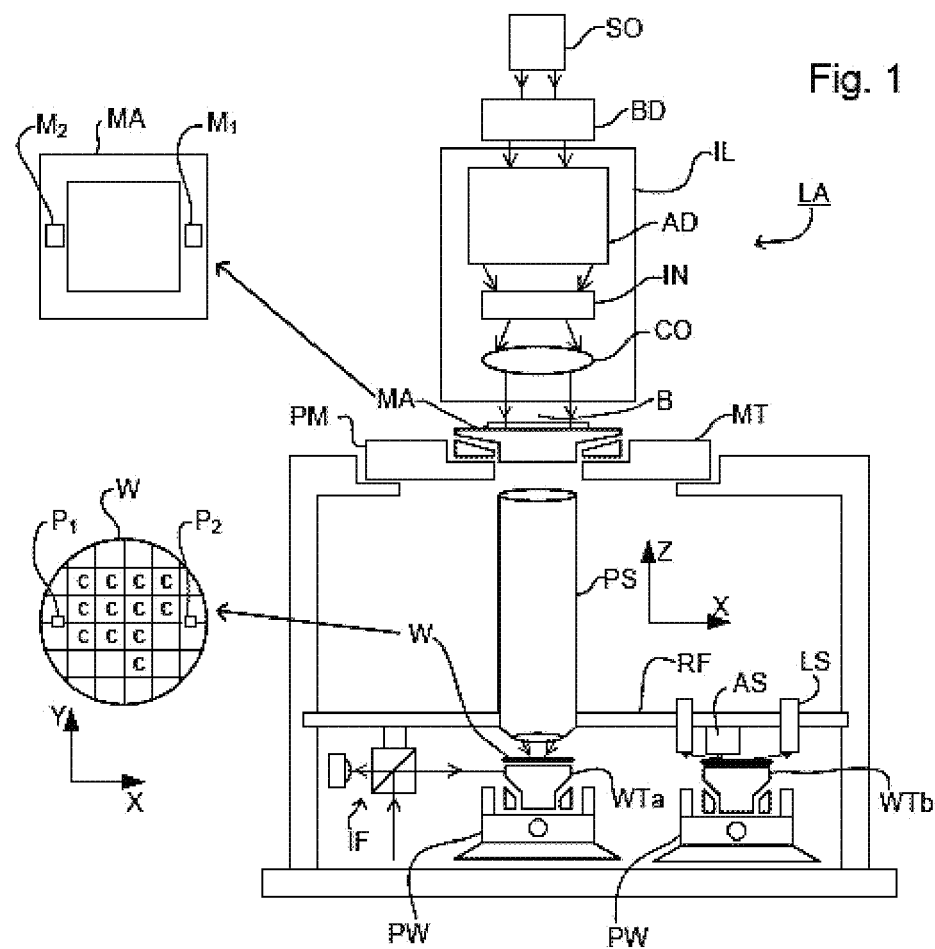
FIG. 1 schematically depicts an embodiment of a lithographic apparatus.

FIG. 1 schematically depicts a lithographic apparatus LA. The apparatus comprises:

an illumination system (illuminator) IL configured to condition a radiation beam B (e.g. UV radiation, DUV radiation or EUV radiation).

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. comprising one or more dies) of the substrate W, the projection system supported on a reference frame (RF).

The illumination system may include various types of optical components, such as refractive, reflective, magnetic, electromagnetic, electrostatic or other types of optical components, or any combination thereof, for directing, shaping, or controlling radiation.

The support structure supports the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more tables (e.g., two or more substrate tables WTa, WTb, two or more patterning device tables, a substrate table WTa and a table WTb below the projection system without a substrate that is dedicated to, for example, facilitating measurement, and/or cleaning, etc.). In such "multiple stage" machines the additional tables may be used in parallel, or preparatory steps may be carried out on one or more tables while one or more other tables are being used for exposure. For example, alignment measurements using an alignment sensor AS and/or level (height, tilt, etc.) measurements using a level sensor LS may be made.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the patterning device and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD configured to adjust the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2.

Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
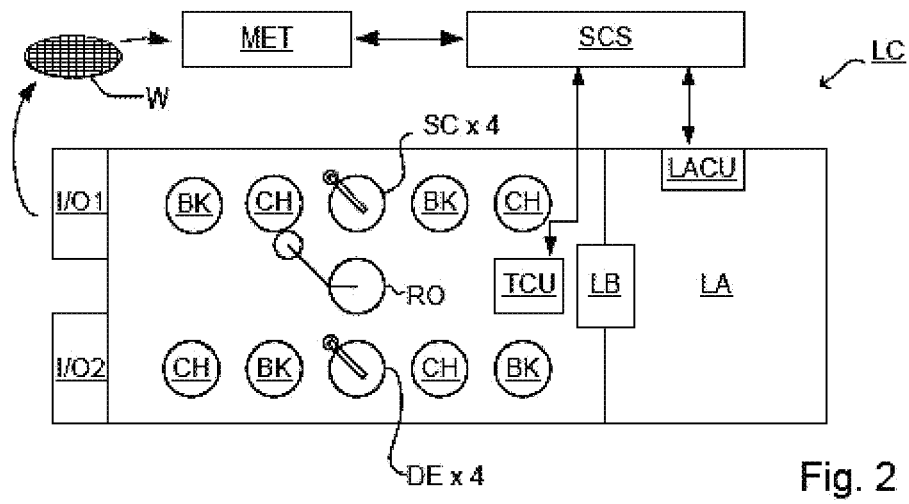
FIG. 2 schematically depicts an embodiment of a lithographic cell or cluster.

As shown in FIG. 2, the lithographic apparatus LA may form part of a lithographic cell LC, also sometimes referred to a lithocell or cluster, which also includes apparatuses to perform pre- and post-exposure processes on a substrate. Conventionally these include one or more spin coaters SC to deposit one or more resist layers, one or more developers DE to develop exposed resist, one or more chill plates CH and/or one or more bake plates BK. A substrate handler, or robot, RO picks up one or more substrates from input/output port I/O1, I/O2, moves them between the different process apparatuses and delivers them to the loading bay LB of the lithographic apparatus. These apparatuses, which are often collectively referred to as the track, are under the control of a track control unit TCU which is itself controlled by the supervisory control system SCS, which also controls the lithographic apparatus via lithography control unit LACU. Thus, the different apparatuses can be operated to maximize throughput and processing efficiency.

In order that a substrate that is exposed by the lithographic apparatus is exposed correctly and consistently, it is desirable to inspect an exposed substrate to measure one or more properties such as overlay error between subsequent layers, line thickness, critical dimension (CD), etc. Accordingly a manufacturing facility in which lithocell LC is located also typically includes a metrology system MET which receives some or all of the substrates W that have been processed in the lithocell. The metrology system MET may be part of the lithocell LC, for example it may be part of the lithographic apparatus LA.

Metrology results may be provided directly or indirectly to the supervisory control system SCS. If an error is detected, an adjustment may be made to exposure of a subsequent substrate (especially if the inspection can be done soon and fast enough that one or more other substrates of the batch are still to be exposed) and/or to subsequent exposure of the exposed substrate. Also, an already exposed substrate may be stripped and reworked to improve yield, or discarded, thereby avoiding performing further processing on a substrate known to be faulty. In a case where only some target portions of a substrate are faulty, further exposures may be performed only on those target portions which are good.

Within a metrology system MET, an inspection apparatus is used to determine one or more properties of the substrate, and in particular, how one or more properties of different substrates vary or different layers of the same substrate vary from layer to layer. The inspection apparatus may be integrated into the lithographic apparatus LA or the lithocell LC or may be a stand-alone device. To enable rapid measurement, it is desirable that the inspection apparatus measure one or more properties in the exposed resist layer immediately after the exposure. However, the latent image in the resist has a low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of a faulty substrate but may still provide useful information.

Figure 3:
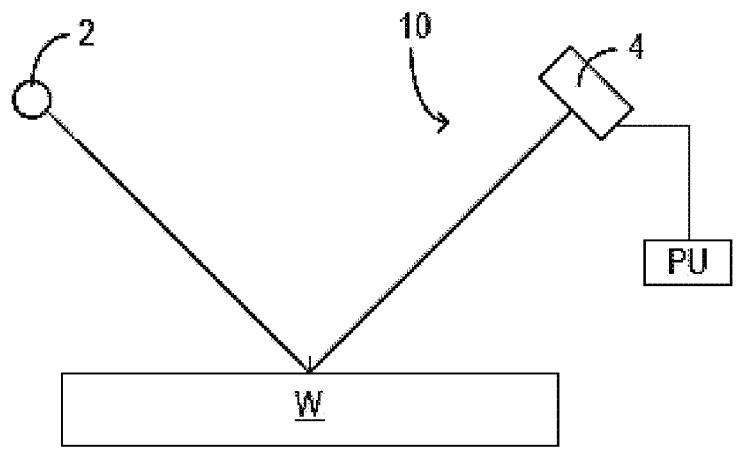
FIG. 3 schematically depicts an example inspection apparatus and metrology technique.
Figure 3:
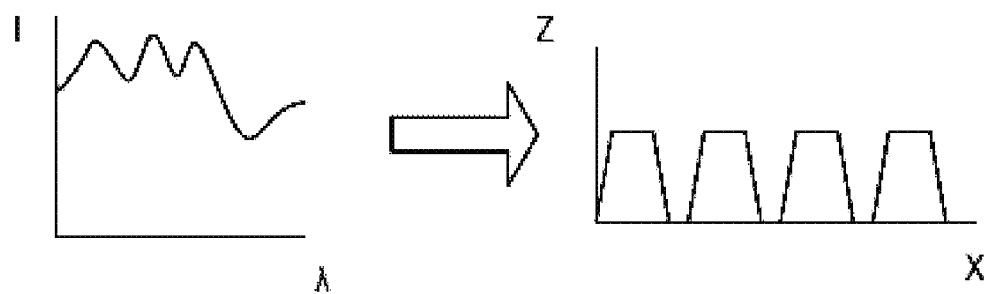

FIG. 3 depicts an example inspection apparatus (e.g., a scatterometer). It comprises a broadband (white light) radiation projector 2 which projects radiation onto a target located, for example, on substrate W. The reflected radiation is passed to a spectrometer detector 4, which measures a spectrum 10 (intensity as a function of wavelength) of the specular reflected radiation, as shown, e.g., in the graph in the lower left. From this data, the structure or profile giving rise to the detected spectrum may be reconstructed by processor PU, e.g. by Rigorous Coupled Wave Analysis and non-linear regression or by comparison with a library of simulated spectra as shown at the bottom right of FIG. 3. In general, for the reconstruction the general form of the structure is known and some parameters are assumed from knowledge of the process by which the structure was made, leaving only a few parameters of the structure to be determined from the measured data. Such an inspection apparatus may be configured as a normal-incidence inspection apparatus or an oblique-incidence inspection apparatus.

Figures 4, 5:
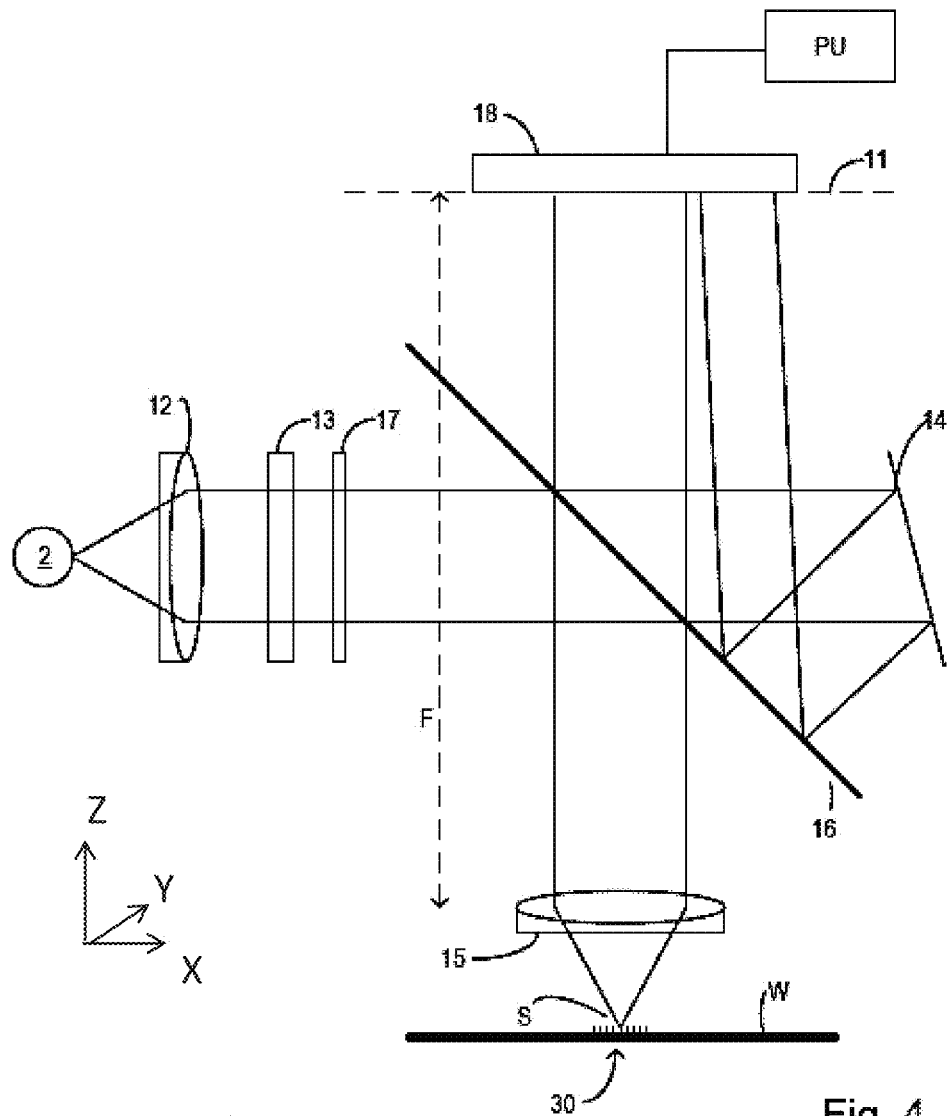
FIG. 4 schematically depicts an example inspection apparatus.
FIG. 5 illustrates the relationship between an illumination spot of an inspection apparatus and a metrology target.

Another inspection apparatus that may be used is shown in FIG. 4. In this device, the radiation emitted by radiation source 2 is collimated using lens system 12 and transmitted through interference filter 13 and polarizer 17, reflected by partially reflecting surface 16 and is focused into a spot S on a target 30 on, e.g., substrate W via an objective lens 15, which has a high numerical aperture (NA), desirably at least 0.9 or at least 0.95. An immersion inspection apparatus (using a relatively high refractive index fluid such as water, or a high refractive index solid located in close proximity of the target) may even have a numerical aperture over 1.

As in the lithographic apparatus LA, one or more substrate tables may be provided to hold the substrate W during measurement operations. The substrate tables may be similar or identical in form to the substrate tables WTa, WTb of FIG. 1. In an example where the inspection apparatus is integrated with the lithographic apparatus, they may even be the same substrate table. Coarse and fine positioners may be provided to a second positioner PW configured to accurately position the substrate in relation to a measurement optical system. Various sensors and actuators are provided for example to acquire the position of a target of interest, and to bring it into position under the objective lens 15. Typically many measurements will be made on targets at different locations across the substrate W. The substrate support can be moved in X and Y directions to acquire different targets, and in the Z direction to obtain a desired location of the target relative to the focus of the optical system. It is convenient to think and describe operations as if the objective lens is being brought to different locations relative to the substrate, when, for example, in practice the optical system may remain substantially stationary (typically in the X and Y directions, but perhaps also in the Z direction) and only the substrate moves. Provided the relative position of the substrate and the optical system is correct, it does not matter in principle which one of those is moving in the real world, or if both are moving, or a combination of a part of the optical system is moving (e.g., in the Z and/or tilt direction) with the remainder of the optical system being stationary and the substrate is moving (e.g., in the X and Y directions, but also optionally in the Z and/or tilt direction).

The radiation redirected by the target then passes through partially reflecting surface 16 into a detector 18 in order to have the spectrum detected. The detector 18 may be located at a back-projected focal plane 11 (i.e., at the focal length of the lens system 15) or the plane 11 may be re-imaged with auxiliary optics (not shown) onto the detector 18. The detector may be a two-dimensional detector so that a two-dimensional angular scatter spectrum of the target 30 can be measured. The detector 18 may be, for example, an array of CCD or CMOS sensors, and may use an integration time of, for example, 40 milliseconds per frame.

A reference beam may be used, for example, to measure the intensity of the incident radiation. To do this, when the radiation beam is incident on the partially reflecting surface 16 part of it is transmitted through the partially reflecting surface 16 as a reference beam towards a reference mirror 14. The reference beam is then projected onto a different part of the same detector 18 or alternatively on to a different detector (not shown).

One or more interference filters 13 are available to select a wavelength of interest in the range of, say, 405-790 nm or even lower, such as 200-300 nm. The interference filter may be tunable rather than comprising a set of different filters. A grating could be used instead of an interference filter. An aperture stop or spatial light modulator (not shown) may be provided in the illumination path to control the range of angle of incidence of radiation on the target.

The detector 18 may measure the intensity of redirected radiation at a single wavelength (or narrow wavelength range), the intensity separately at multiple wavelengths or integrated over a wavelength range. Furthermore, the detector may separately measure the intensity of transverse magnetic- and transverse electric-polarized radiation and/or the phase difference between the transverse magnetic- and transverse electric-polarized radiation.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may be etched into or on the substrate (e.g., into one or more layers on the substrate). The pattern (e.g., of bars, pillars or vias) is sensitive to optical aberration in the lithographic projection apparatus, particularly the projection system PS, and illumination symmetry and the presence of such aberration will manifest in a variation in the printed grating. Accordingly, the measured data of the printed grating is used to reconstruct the grating. One or more parameters of the 1-D grating, such as line width and/or shape, or one or more parameters of the 2-D grating, such as pillar or via width or length or shape, may be input to the reconstruction process, performed by processor PU, from knowledge of the printing step, material deposition and/or etching processes, and/or other inspection processes.

In addition to measurement of a parameter by reconstruction, angle resolved scatterometry is useful in the measurement of asymmetry of features in product and/or resist patterns. A particular application of asymmetry measurement is for the measurement of overlay, where the target 30 comprises one set of periodic features superimposed on another. The concepts of asymmetry measurement using the instrument of FIG. 3 or FIG. 4 are described, for example, in U.S. patent application publication US 2006-066855, which is incorporated herein in its entirety. Simply stated, while the positions of the diffraction orders in the diffraction spectrum of the target are determined only by the periodicity of the target, asymmetry in the diffraction spectrum is indicative of asymmetry in the individual features which make up the target. In the instrument of FIG. 4, where detector 18 may be an image sensor, such asymmetry in the diffraction orders appears directly as asymmetry in the pupil image recorded by detector 18. This asymmetry can be measured by digital image processing in unit PU, and calibrated against known values of overlay.

FIG. 5 illustrates a plan view of a typical target 30, and the extent of illumination spot S in the apparatus of FIG. 4. To obtain a diffraction spectrum that is free of interference from surrounding structures, the target 30, in an embodiment, is a periodic structure (e.g., grating) larger than the width (e.g., diameter) of the illumination spot S. The width of spot S may be smaller than the width and length of the target. The target in other words is 'underfilled' by the illumination, and the diffraction signal is essentially free from any signals from product features and the like outside the target itself. The illumination arrangement 2, 12, 13, 17 may be configured to provide illumination of a uniform intensity across a back focal plane of objective 15. Alternatively, by, e.g., including an aperture in the illumination path, illumination may be restricted to on axis or off axis directions.

But, there is demand to reduce the space occupied by metrology targets. For example, there is a desire to reduce the width of 'scribe lanes' between target portions C on the substrate, where metrology targets have conventionally been located. Additionally or alternatively, there is a desire, for example, to include metrology targets within the device patterns themselves, to allow more accurate and/or precise monitoring and correction of variations in parameters such as CD and/or overlay. To this end, alternative methods of diffraction based metrology have been devised more recently. For example, in image-based metrology, two images of the target are made, each using different selected orders of the diffraction spectrum. Comparing the two images, one can obtain asymmetry information. By selecting parts of the images, one can separate the target signal from its surroundings. The targets can be made smaller, and need not be square, so that several can be included within the same illumination spot. Examples of this technique are described in U.S. patent application publications US2011-0027704, US2011-0043791, and US2012-0044470.

In addition to or alternatively to reducing the space occupied by metrology targets, there is demand to improve the nature of the measurements themselves, such as their accuracy and/or precision. For example, there is a desire to, for example, obtain higher sensitivity of measurement. Additionally or alternatively, there is a desire to, for example, obtain better decoupling between various parameters in, e.g., the reconstruction described above. For example, it is desired to obtain better values for each of the specific parameters of interest, by reducing or eliminating the effect of measurements associated with one parameter of interest influencing another parameter of interest.

As the demand for size reduction and/or accuracy/precision continues, existing techniques may meet some technical limitations. For example, some methods desire to capture at least the $\pm 1^{st}$ diffraction orders. Taking into account the numerical aperture of the objective 15, this constrains the pitch (L) of a periodic structure of the target. To improve sensitivity and/or to reduce target size, one can consider using shorter wavelengths $\lambda$. Further, the target cannot be too small otherwise it will not have enough features to be considered as a periodic structure. Consequently, overlay, as an example, is measured using periodic structures features (e.g., lines) having dimensions far bigger than those of the product (e.g., device) layout, making overlay measurement less reliable. Ideally the feature line and pitch should have similar dimensions to the product features.

Figure 6:
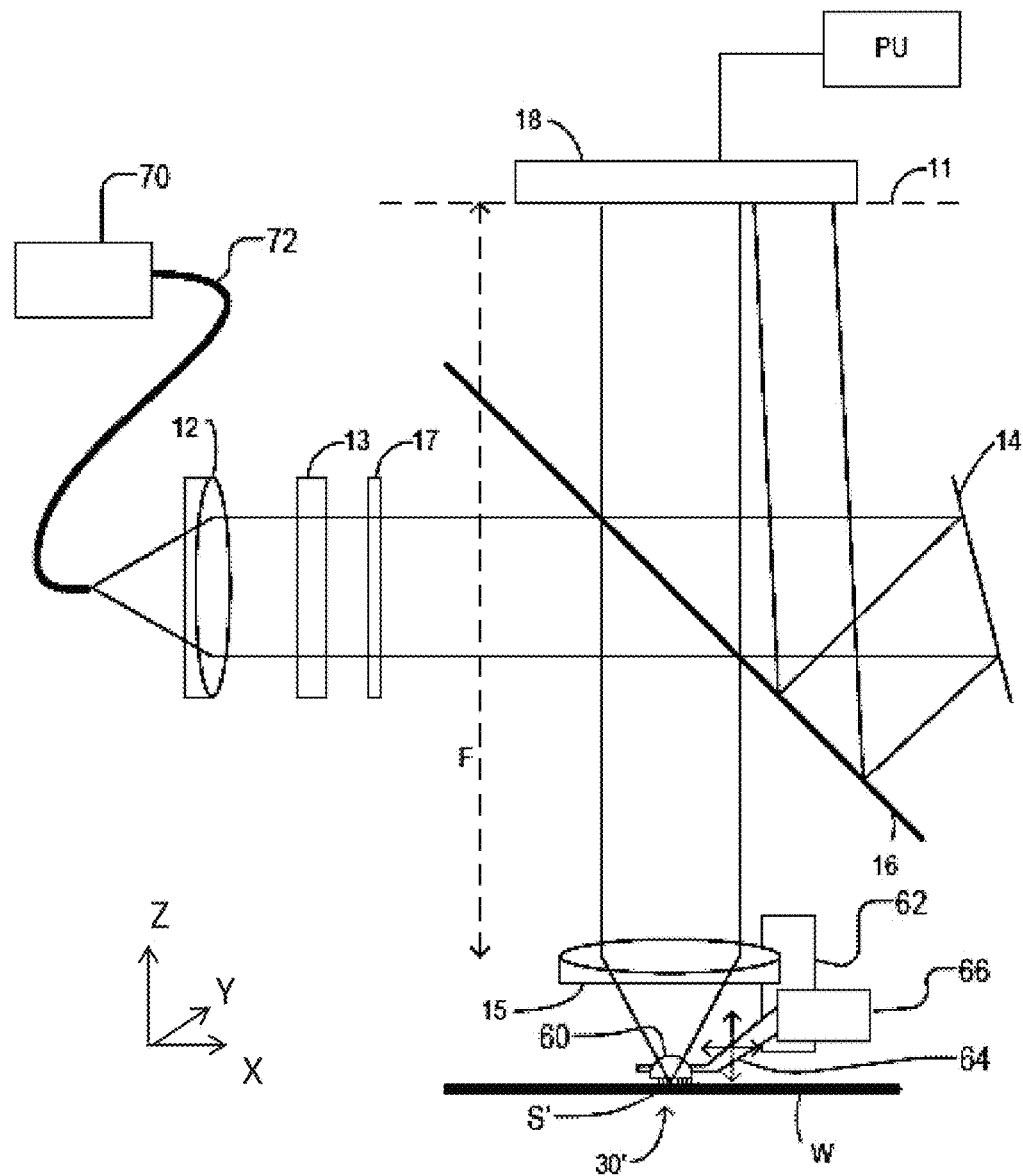
FIG. 6 depicts an example inspection apparatus comprising a solid immersion lens (SIL)

FIG. 6 shows an inspection apparatus in which improvement of the nature of the measurements themselves (e.g., accuracy and/or precision) and/or reduction of target size may be realized. In FIG. 6, a spot S' (which may be smaller than convention if, for example, a smaller target is desired) can be applied to a target 30' (which may be smaller than convention, e.g., features of smaller pitch, if, for example, a smaller target is desired).

Comparing the apparatus of FIG. 6 with that of FIG. 4, a first difference is the provision of an additional optical element 60 close to the target 30'. In an embodiment, this additional optical component is a miniature solid immersion lens (SIL), with a width (e.g., diameter) only on the order of millimeters, for example in the range of 1 mm to 5 mm, for example about 2 mm. The SIL comprises, in an example, a hemisphere of material that receives rays of radiation at substantially normal incidence to its surface. In an embodiment, the SIL may be a different shape such as a super-hemisphere. In an embodiment, the SIL is made up of a material of refractive index n, such as glass, a crystal, fused quartz, a combination of materials, a coated element (e.g. the coating material is different than the material of the element), etc. In an embodiment, the refractive index n is relatively high, e.g., greater than or equal to about 1.5, greater than or equal to about 1.8, greater than or equal to about 2, greater than or equal to about 2.2, or greater than or equal to about 3.5 (e.g., near-infrared with a SIL of GaP material). Within the SIL material, the numerical aperture (NA) of the original rays is increased. The received rays come to focus at about the center of the hemisphere or the aplanatic point of a super-hemisphere and form a spot that is smaller by a factor of n (for a hemisphere) or $n^2$ (for an aplanatic super-hemisphere) compared to what would have been in the absence of the SIL. For example, a typical glass hemisphere having n=2 will reduce the width of the focused spot by a factor of 2. In an embodiment, the tip of the SIL 60 may be in the form of a truncated cone, stepwise protrusion or pyramid shape with a generally flat surface, at the apex side, facing towards the target.

When an objective of numerical aperture $NA_o$ focuses inside a hemispherical SIL, the numerical aperture of the combined system becomes $NA=n_{SIL} NA_o$ inside the SIL, where $n_{SIL}$ is the refractive index of the SIL. With, for example, a high NA objective of $NA_o=0.9$ and a SIL with $n_{SIL}=2$, a hyper-NA value of NA=1.8 may be achieved; while, an alternative more-than-hemispherical SIL design in combination with a high NA objective can result in a hyper-NA value of $NA=n_{SIL}^2 NA_o$. Such a hyper-NA optical configuration can improve the metrology capability of an inspection apparatus when the distance between the SIL and the target is significantly less than the wavelength of the radiation used or when a refractive index matching liquid is used.

When the distance between the SIL and the target 30 (such as one or more structured or unstructured layers deposited on substrate W) exceeds approximately half a wavelength of the radiation beam (whether a beam for inspection of the target, a beam for position measuring, etc.), then rays that are focused inside the SIL 60 at angles $\alpha$ to the optical axis with $n_{SIL} \sin \alpha > 1$ are fully reflected at the planar interface of the SIL tip and an environment (e.g., gas such as air) between the tip and the surface W with a refractive index of about 1, by total internal reflection (TIR). Thus, TIR limits the effective numerical aperture of the illumination of the surface W to about 1 and so also limits the NA to the same value for the detection of the radiation redirected by the target. However, when the distance between the SIL and the surface is significantly less than half the wavelength $\lambda$ (e.g., less than approximately $\lambda/10$), strong evanescent coupling between the $n_{SIL} \sin \alpha > 1$ rays and the surface W occurs. This evanescent coupling enables the $n_{SIL} \sin \alpha > 1$ rays to carry information of the surface W and increases the effective numerical aperture for illumination and detection to, e.g., about 1.8 as described above. This phenomenon is known as frustrated total internal reflection (FTIR) or evanescent coupling. In such a case, the SIL and the surface W may be considered as being in optical contact without being in actual mechanical contact. Therefore, under FTIR conditions, illumination of a surface W and detection of the radiation redirected by the surface W is possible with values for the numerical aperture exceeding 1 (hyper-NA).

Immersion of optical elements in liquid has been used to increase resolution in microscopy and photolithography. The solid immersion lens may achieve similar gains, or even larger gains, without the inconvenience/problems of liquid immersion. However, to ensure that the increased NA does indeed increase the resolution of the system, the bottom of the SIL must either be in contact with the target 30 or positioned extremely closely to it.

A so-called micro-SIL may also be used. The width (e.g., diameter) of such a SIL is many times smaller, for example about 2 microns in width instead of about 2 millimeters. In an example where SIL 60 in the FIG. 6 apparatus is a micro-SIL, it may have a width (e.g., diameter) less than or equal to 10 µm, potentially less than or equal to 5 µm.

Whether a miniature or micro-SIL 60 is used, it can be attached to a movable support so that controlling the alignment and proximity to the target is much simpler than in the case of a lens with bigger width. For example, the SIL 60 in FIG. 6 is mounted to a frame 62. In an embodiment, frame 62 is movable. An actuator may be provided to move frame 62. In an embodiment, the frame 62 supports the objective 15. Accordingly, in an embodiment, the frame 62 may move both the objective 15 and the SIL 60 together. In an embodiment, the actuator for the frame 62 may be configured to move the frame 62 (and the SIL 60) in substantially the Z direction. In an embodiment, the actuator for the frame 62 may be configured to move the frame 62 (and the SIL 60) around the X axis and/or Y axis. In an embodiment, the SIL 60 is in relative fixed position relative to the frame 62. This may be referred to a single stage arrangement, where the objective 15 and SIL 60 are fixed relative to each and are moved by the actuator of frame 62. In such a case, a benefit may be that the SIL can be mechanically positioned in the focus of the objective.

As noted above, the SIL 60 in FIG. 6 is mounted to a frame 62, which in an embodiment supports objective 15. Of course, the SIL 60 may be mounted on a separate frame from that supporting objective 15. In an embodiment, the SIL 60 is connected to a frame (e.g., frame 62) via a structure 64 and actuator 66. Actuator 66 may be, for example, piezoelectric in operation or voice coil actuated. The arrangement where the SIL 60 has an actuator to cause relative movement between a movable objective 15 and the SIL 60 may be referred to as a dual stage arrangement. In a dual stage, certain functionalities may be separated, e.g. separation of motion ranges, vibration suppression capabilities, SIL positioning and focusing with respect to the surface. For example, the (relatively large) objective stage comprises the relatively heavy objective and can have relatively large motion range. In an embodiment, the objective stage may move only substantially in the Z-direction (substantially/ essentially normal to the surface). Further, it can have a certain bandwidth (e.g., ~100 Hz) sufficient for relatively long displacement ranges, but perhaps not sufficient (e.g., too low bandwidth) for suppression of small position disturbances. The (relatively small) SIL stage comprises the relatively light SIL and can have a relatively small motion range. In an embodiment, the SIL stage may move in more than 1 degree of freedom, e.g., at least 3 degrees of freedom, e.g., in the Z-direction and around the X-axis and/or the Y-axis, to position the SIL substantially/essentially parallel to the surface. Further, it can have a certain bandwidth (e.g., sufficiently high) to suppress small position disturbances (e.g., up to several hundreds of nanometers). The SIL stage may not have a mechanical range sufficient to cover the desired full travel range. So, the SIL stage can be used to position the SIL at a certain small distance (e.g., about 10-100 nm, or about 10-50 nm) above the surface, while the objective stage can position the objective at focus with respect to the surface, or with respect to the SIL.

Actuator 66 may operate in combination with one or more other actuators positioning the objective as a whole in relation to the target. In relation to the coarse and fine positioners mentioned above, for example, the actuator 66 may be regarded as an ultra-fine positioner. The control loops of these different positioners can be integrated with one another. The components 62, 64 and 66, together with the substrate table and positioners (mentioned above but not shown in FIG. 6), form a support apparatus for positioning the SIL and the target 30 in close proximity to one another. As noted above, in principle, SIL 60 could be mounted rigidly to the frame 62, and/or may be of larger width. The separate structure and actuator allows easier control of the very small gap, as discussed in more detail below.

Inclusion of the SIL 60 opens the possibility of, for example, focusing to a much smaller spot S'. The SIL works by illuminating the target with both propagating and evanescent waves and capturing the near-field radiation (including waves that are evanescent in the gap) from the target, and to this end it is positioned substantially closer than one wavelength ($\lambda$) of radiation from the target structure, generally closer than a half wavelength, for example around $\lambda/20$. The closer the distance, the stronger will be the coupling of near-field signals into the instrument. The gap between the SIL 60 and target 30' may therefore be less than 100 nm, for example between 10 nm and 100 nm or between 10 nm and 50 nm.

Because the NA of the inspection apparatus is effectively increased, the sensitivity and parameter de-correlation is enhanced such that the pitch of the target periodic structure may be reduced. That is, with, e.g., decreasing size of device features produced by a lithographic process, the pitch of the periodic structure of the metrology target may be reduced so that, e.g., it more accurately represents the decreased size of device features. This periodic structure pitch shrink may increasingly cause parameters of the periodic structure to become correlated in the detected radiation distribution from the periodic structure. This means that, for two different parameters of the periodic structures, changes in the detected radiation distribution due to a small change in these parameters of the periodic structure become increasingly similar. This can cause the performance of the metrology apparatus (e.g., the results of determining of one or more parameters of interest from analysis of the detected radiation distribution) to decrease with decreasing pitch of the periodic structure of the metrology target. In addition or alternatively, the detected intensity noise may also increase with decreasing pitch and so cause the performance of the metrology apparatus (e.g., the results of determining of one or more parameters of interest from analysis of the detected radiation distribution) to decrease. Thus, the precision with which one or more dimensions and/or optical parameters of a metrology target periodic structure are reconstructed is limited by signal to noise of the detected radiation distribution and parameter cross correlation.

In examples where a micro-SIL would be used, spatially incoherent radiation of the type conventionally used in, for example, a scatterometer cannot be focused to a micron-sized spot as small as the micro-SIL. Accordingly, in such an embodiment or in an embodiment using a macro-SIL (i.e.; one larger than a micro-SIL) the radiation source 2 may be changed to a spatially coherent source. Therefore a laser source 70 is coupled to illumination optics 12, etc. via an optical fiber 72. The limit on the spot size on the target is set by the numerical aperture of the focusing lens system and the laser wavelength. As an additional benefit of using spatially coherent radiation, the instrument with laser radiation source 70 can be used to perform different types of scatterometry or measurement. For example, coherent Fourier scatterometry (CFS) may be used to measure the target.

As highlighted above, a small gap (e.g., a value in the range of 10-100 nm, e.g., about 20, 25, 30, 35, 40, 45, 50, 55, 60, 65, 70, 75, 80 or 85 nm) should be maintained between the SIL and the target.

Figure 7:
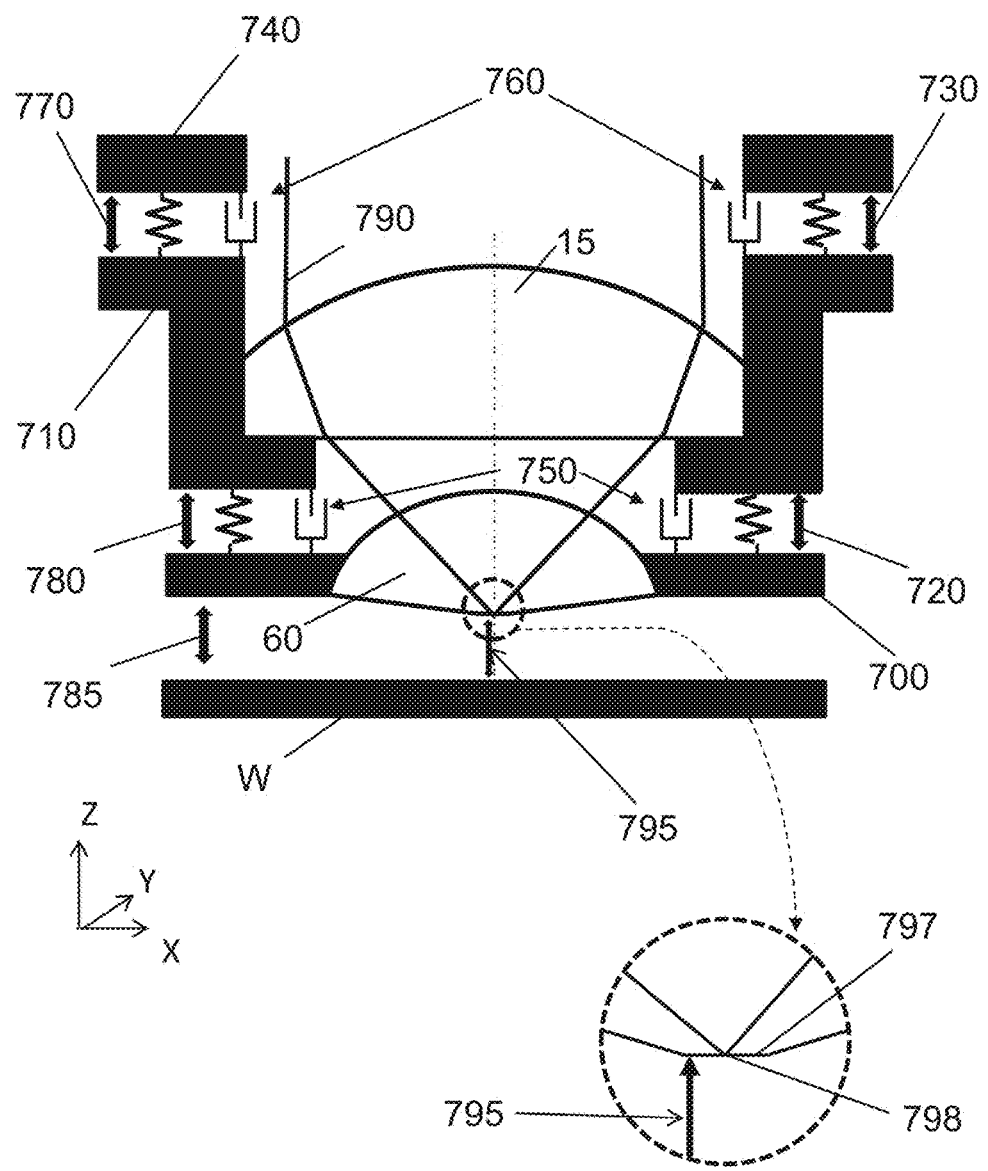
FIG. 7 depicts a schematic diagram of specific components of an inspection apparatus in relation to a target surface.

As noted above, a "dual stage" concept may be used to facilitate positioning of the SIL and the objective close to the measured surface and allows for certain functionalities to be separated, e.g. separation of motion ranges, vibration suppression capabilities, SIL positioning and/or focusing with respect to the surface. Referring to FIG. 7, an embodiment of a "dual stage" concept is schematically depicted. A SIL 60 is attached to a movable support 700 to facilitate controlling the alignment and proximity of the SIL 60 to the measured surface, in this case the substrate W. This may be termed the SIL stage. Further, an objective 15 is attached to a movable support 710 to facilitate controlling the alignment and proximity of the SIL 60 and the objective 15 to the measured surface, in this case the substrate W. This may be termed the objective stage.

An actuator 720 may be provided to move the movable support 700 and the SIL 60 with respect to the movable support 710 and/or objective 15. An actuator 730 may be provided to move the movable support 710 and objective 15 with respect to a support 740. In this embodiment, the movable support 700 is mounted on the movable support 710 and so movement of the movable support 710 may also cause the movable support 700 and/or the SIL 60 to move. Accordingly, in an embodiment, the movable support 710 may move both the objective 15 and the SIL 60 together. Actuator 720 and/or 730 may be, for example, piezoelectric in operation or voice coil actuated.

The SIL stage may be mechanically suspended relative to the objective stage, which is represented by an equivalent spring and/or damping 750. The spring and/or damping 750 may be incorporated in the actuator 720 and/or provided separately by appropriate spring and/or damper structure. Similarly, the objective stage may be mechanically suspended relative to the support 740, which is represented by an equivalent spring and/or damping 760. The spring and/or damping 760 may be incorporated in the actuator 730 and/or provided separately by appropriate spring and/or damper structure.

In an embodiment, the actuator 720 may be configured to move the movable support 700 (and the SIL 60) in substantially the Z direction. In an embodiment, the actuator 720 may be configured to move the movable support 700 (and the SIL 60) around the X axis and/or Y axis. In an embodiment, the actuator 730 may be configured to move the movable support 710 (and the objective 15) in substantially the Z direction. In an embodiment, the actuator 730 may be configured to move the movable support 710 (and the objective 15) around the X axis and/or Y axis. In an embodiment, the objective stage may move only substantially in the Z-direction (substantially normal to the surface). In an embodiment, the SIL stage may move in more than 1 degree of freedom, e.g., at least 3 degrees of freedom, e.g., in the Z-direction and around the X-axis and/or the Y-axis, to position the SIL substantially parallel to the surface. The SIL stage may not have a mechanical range sufficient to cover the desired full travel range. So, the SIL stage can be used to position the SIL at a certain small distance above the surface, while the objective stage can position the objective at focus with respect to the surface, or with respect to the SIL.

Further, in an embodiment, the surface W itself may be moved. For example, a substrate table WT having the surface W may move the surface W relative to the SIL 60 to facilitate establishing an appropriate gap between the SIL 60 and the surface W.

To enable such positioning, one or more signals may be provided. For example, one or more signals 770 may be provided to enable positioning of the objective 15 and/or SIL 60 relative to the support 740 and/or to the surface W. Similarly, one or more signals 780 may be provided to enable positioning of the SIL 60 relative to the objective 15 and/or to the surface W. One or more signals 785 may be provided to enable positioning of the SIL 60 relative to the surface W. As an example, a signal 770 to enable relative positioning between the objective 15 and the support 740 may be provided by an encoder, a gas sensor, or an interferometer.

A signal 770 to enable relative positioning between the objective 15/SIL 60 and the surface W may be a signal derived from a radiation beam 790 passing through the objective 15, the SIL 60 and onto the surface W. As shown in the inset of FIG. 7, the radiation beam 790 may have a focus 798 located at the tip 797 of the SIL 60. In an embodiment, the tip 797 of the SIL 60 comprises a planar surface. The radiation beam 790 may be a dedicated beam for determining the position or may be the beam used to measure the surface but used for a certain time as a position measuring beam. A signal 780 to enable relative positioning between the objective 15 and the SIL 60 may be a focus error signal (FES). A signal 785 to enable relative positioning between the SIL 60 and the surface W may be a gap error signal (GES) as described herein.

So, the actuators 720 and 730 may operate in combination to position the objective 15 and the SIL 60 in relation to the surface W to establish a desired gap 795. A control system is provided to control positioning of the SIL 60 close to the surface W and to maintain the SIL 60 at or around that position. The control system may receive a setpoint gap value and control one or more actuators (e.g., actuators 720 and/730) to position, in one or more motions, the SIL 60 at or near the setpoint gap value and maintain the SIL 60 at or around that position. There may be significant relative vibrations between the surface W and the SIL 60. So, the SIL 60 may be controlled via a high-bandwidth (e.g., 1-10 kHz) feedback control system. To enable the control by the control system, the gap between the SIL 60 and the surface W may be represented by one or more signals, e.g., a gap error signal (GES). Various techniques for measuring the GES or other position signals are known in the art.

In an embodiment, the actuator 720 may be considered a fine positioner and the actuator 730 may be considered a coarse positioner. In an embodiment for motion in the Z-direction (e.g., vertical motion), a "dual stage" system may enable control of both the (1) focus between the objective 15 and the SIL 60, and (2) the gap 795 between the SIL 60 and the surface W.

Figure 8:
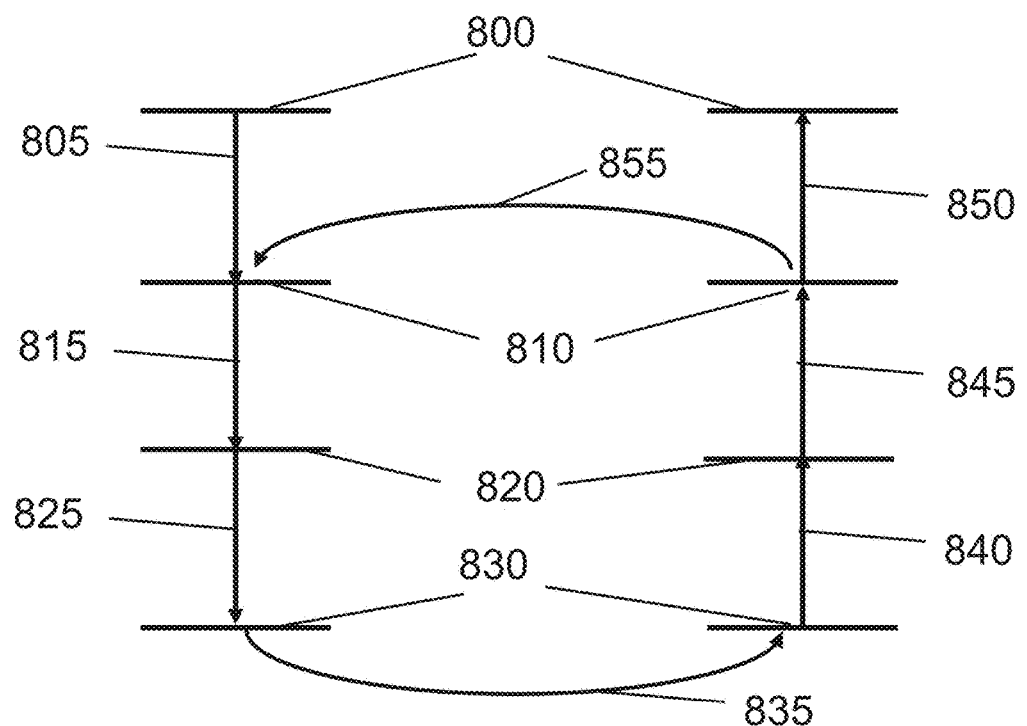
FIG. 8 depicts a schematic representation of various setpoints for relative positioning of various specific components of an inspection apparatus in relation to a target surface.

Further, a "dual stage" system can enable a relatively large dynamic range for the gap 795, e.g., about mm range (with sub-mm accuracy) to about sub-100 nm range (with sub-10 nm accuracy). Referring to FIG. 8, an embodiment of Z-direction motion set points is schematically described. A first setpoint distance 800 may be defined for the distance of the SIL 60 from the surface W (i.e., gap 795) to enable exchange of a surface to be measured (e.g., substrate W) with another surface to be measured. In an embodiment, the first setpoint distance 800 may be selected from the range of about several millimeters, e.g., about 1-5 mm, or about 1 mm. Once a surface W to be measured is in place, the SIL 60 may be positioned closer to the surface W in an approach motion 805 to a second setpoint distance 810 of the gap 795. In an embodiment, the second setpoint distance 810 may be selected from the range of about several hundreds of microns down to several tens of microns, e.g., 400 to 50 microns, e.g., about 150 to 350 microns, e.g., about 300 microns. The second setpoint distance 810 enables relatively safe relative movement between the surface W and the SIL 60, for example, to horizontally position the SIL 60 over a target 30.

From the second setpoint distance 810, the SIL 60 may be positioned closer to the surface W in an approach motion 815 to a third setpoint distance 820 of the gap 795. In an embodiment, the third setpoint distance 820 may be selected from the range of half a wavelength, e.g., about 350 to 100 nanometers, e.g., about 350 to 175 nanometers, e.g., about 300 nanometers. The third setpoint distance 820 may be the maximum gap 795 for which a particular signal may be used and/or the point at which a different approach velocity/acceleration is used.

From the third setpoint distance 820, the SIL 60 may be positioned closer to the surface W in an approach motion 825 to a fourth setpoint distance 830 of the gap 795. In an embodiment, the fourth setpoint distance 830 may be selected from the range of about 100 to 10 nanometers, e.g., about 50 to 10 nanometers, e.g., about 20-30 nanometers or about 30 nanometers. The fourth setpoint distance 830 may be the gap 795 at which the measurement is taken 835. In an embodiment, during the measurement, the gap 795 is substantially maintained at the fourth setpoint distance 830.

As discussed further below in respect of parameter decorrelation, in an embodiment, there may be a plurality of fourth setpoint distances 830, at each of which a measurement may be taken. Or, one or more fourth setpoint distances 830 may be respectively a starting point and/or end point for a relative motion between the SIL 60 and the target (whether a motion apart from each other or toward each other) during at least part of which motion a plurality of measurements are taken. In an embodiment, there may be a combination of one or more fourth setpoint distances 830 at which a measurement is taken and one or more fourth setpoint distances 830 that are respectively a starting point and/or end point for a relative motion between the SIL 60 and the target during at least part of which motion a plurality of measurements are taken.

Once the measurement is complete, the SIL 60 is positioned further away from the surface W to either enable a further measurement at another location on the surface or exchange of the surface W for another surface W. In an embodiment, the SIL 60 is positioned further away from the surface W in a retraction motion 840 to a third setpoint distance 820, which may have the same value as for the approach motion 825 or may be different therefrom. From the third setpoint distance 820, the SIL 60 is positioned further away from the surface W in a retraction motion 845 to a second setpoint distance 810, which may have the same value as for the approach motion 815 or may be different therefrom.

As noted above, the SIL 60 may be maintained at the second setpoint distance 810 to enable relatively safe relative movement 855 between the surface W and the SIL 60 to, e.g., horizontally position the SIL 60 over a further target 30 by relative movement between the SIL 60 and the target (e.g., moving the surface W horizontally and/or moving the SIL 60 horizontally). So, in an embodiment, for each target at a different location on the surface W, the approach motions 815 and 825 and retraction motions 840 and 845 of the SIL is repeated to help avoid damage of the surface W and the SIL 60 during relative lateral motion between the SIL 60 and the surface W. In an embodiment, the retraction motions 840 and 845 may be combined into a single motion to the second setpoint distance 810, where, for example, the next operation is relative lateral movement 855 between the surface W and the SIL 60 to position the SIL 60 over a further target 30.

If the surface W is being replaced with another surface W or the sensor is being shut down, the SIL 60 is positioned further away from the surface W in a motion 850 to a first setpoint distance 800, which may have the same value as for the start of the motion 805 or may be different therefrom. In an embodiment, the motions 840, 845 and 850 may be combined into a single motion to the first setpoint distance 800, where, for example, the next operation is the surface W being replaced with another surface W or the sensor being shut down.

In an embodiment, the approach motion 805 need not have the same parameters (e.g., acceleration, speed, setpoint, etc.) as the retraction motion 850. Similarly, in an embodiment, the retraction motion 845 need not have the same parameters (e.g., acceleration, speed, setpoint, etc.) as the approach motion 815. Similarly, in an embodiment, the retraction motion 840 need not have the same parameters (e.g., acceleration, speed, setpoint, etc.) as the approach motion 825.

As discussed above, a parameter of interest (e.g., critical dimension (CD), overlay, dose, focus, alignment, etc.) of a lithography target may be determined using radiation-based metrology (e.g., scatterometry) with a solid immersion lens (SIL). The lower surface of the SIL (SIL tip) is kept at a small distance (e.g., a gap in the range of 10-50 nanometers) from the target. The radiation redirected from the target, via the SIL tip, forms an intensity distribution (intensity pupil) in, e.g., the back-focal plane of an objective lens, which is imaged onto and measured using a detector (e.g., a CCD camera). The radiation distribution in the measured pupil depends on the size of the gap and the geometrical and optical properties of the target that is measured.

In an embodiment, the inspection apparatus may operate with visible light despite the fact that the periodic structure of the target is beyond the imaging resolution limit in visible light. Therefore, a target periodic structure may not be imaged directly.

Thus, in an embodiment, a reconstruction of one or more geometrical (e.g., bottom CD, top CD, side wall angle, height, etc.) and/or optical parameters of the target is computed based on the measured radiation distribution (e.g., angular resolved intensity radiation distribution) that is detected in the back focal plane (or a conjugate thereof) of the objective lens. As noted above, this radiation distribution may be referred to as a pupil.

Figure 9:
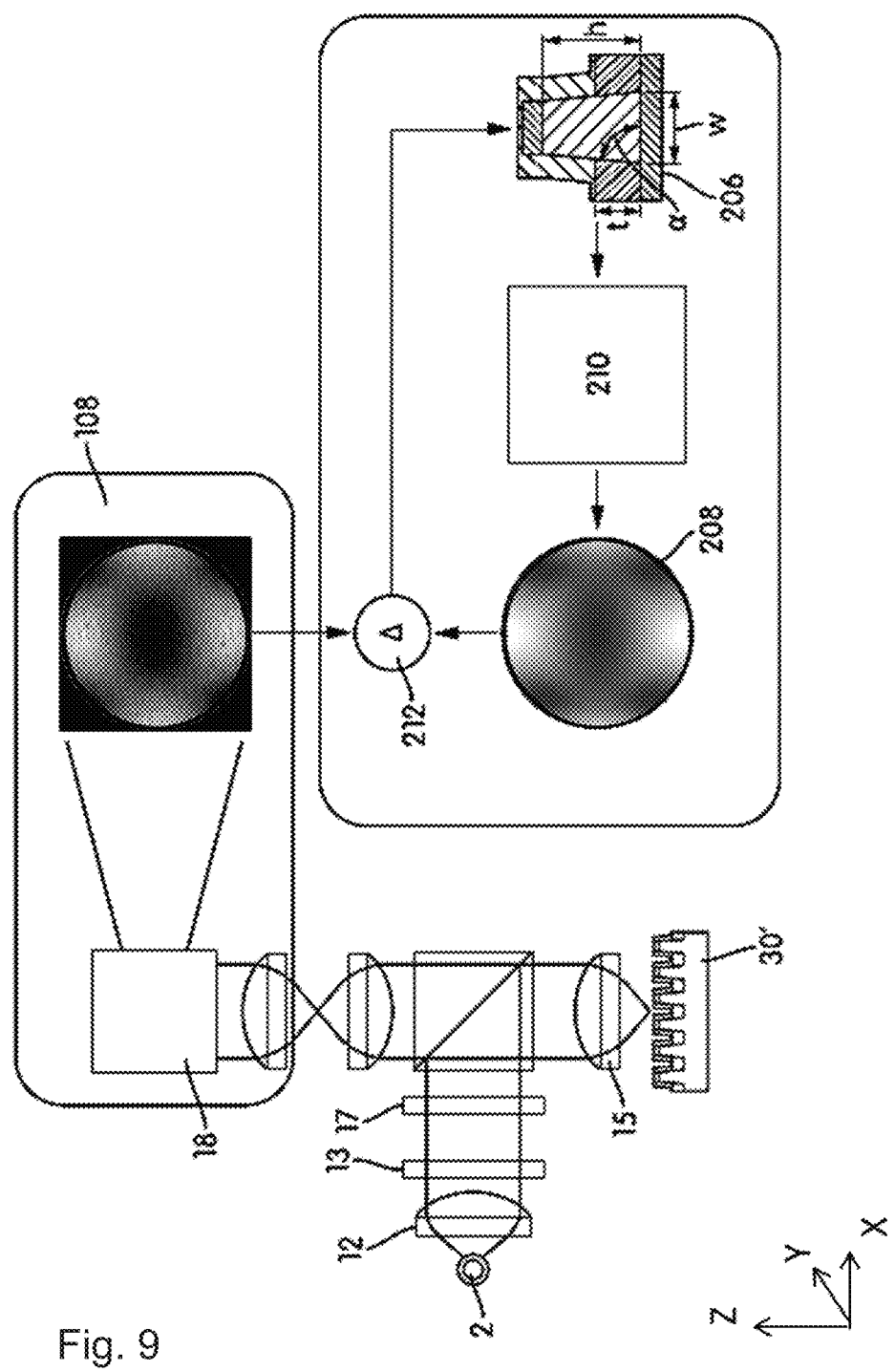
FIG. 9 schematically depicts a process of deriving a parameter of interest based on measurement data.
Figure 10:
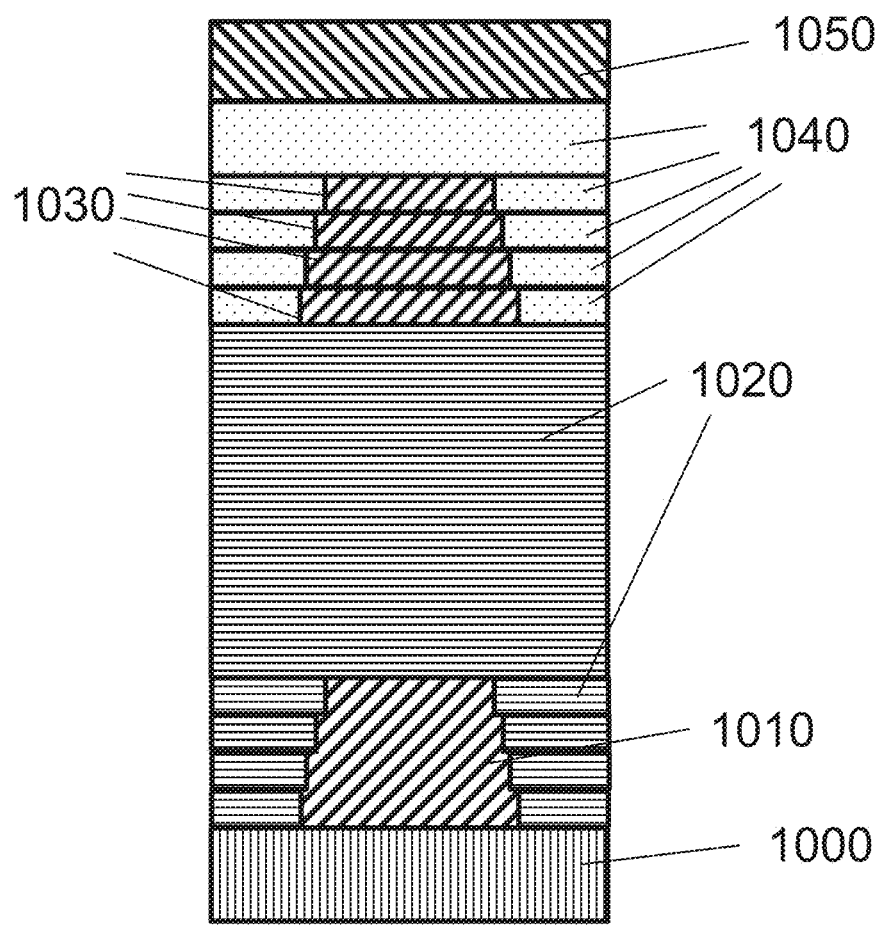
FIG. 10 schematically depicts an example unit cell model of a feature of a periodic structure of a target.

FIG. 9 schematically depicts an example process of the determination of one or more parameters of interest of a target pattern based on measurement data obtained using metrology. Radiation detected by detector 18 provides a measured radiation distribution 108 for target 30'. This measured radiation distribution 108 contains information to enable derivation of a parameter of interest such as the overlay error between successive layers formed in or on the substrate and/or critical dimension of, e.g., developed photosensitive resist. FIG. 10 depicts an example unit cell model of a portion of a target (such as target 30, 30') and example layers of various materials making up, and associated with, the target. For example, the target may comprise a layer of silicon nitride ($Si_3N_4$) represented by segment 1010, which layer may form a grating feature, overlying, e.g., a bare silicon substrate or other layer represented by segment 1000. Overlying layer 1010 may be a layer of TEOS (tetraethyl orthosilicate) represented by segment 1020. Overlying layer 1020 is a further layer of silicon nitride ($Si_3N_4$) represented by one or more segments 1030, which may form a further grating feature (e.g., a grating feature for measuring overlay). Overlying layer 1030 is a vacuum or non-solid medium gap represented by one or more segments 1040, such as gas (e.g., air). And, further overlying layer 1030 is an optical element, represented by segment 1050, from which radiation emanates, through the vacuum/medium 1040, toward the layer 1030. In FIG. 10, the layer 1030 and vacuum/medium 1040 are shown segmented in to a plurality of segments to facilitate calculation, while in reality the layer 1030 and/or vacuum/medium 1040 is typically continuous. Similarly, layers 1050, 1020, 1010 and 1000 are represented by a single segment, but may be represented by a plurality of segments. Also, layer 1050 may represent only a part of the complete shape of the optical element, which can be, e.g., hemispherical.

For a given target 30', a radiation distribution 208 can be computed/simulated from a parameterized model 206 (such as the unit cell of FIG. 10) of the pattern for target 30' using, for example, a numerical Maxwell solver 210. The parameterized model 206 may include one or more of the parameters of the segments identified in FIG. 10, such as the thickness of one or more layers, the refractive index (e.g., a real or complex refractive index, refractive index tensor, etc.) of one or more of the layers, a sidewall angle of one or more layers, absorption of one or more layers, etc., as well as of any portions thereof (such as one or more portions or combinations of portions) such as the segments identified for the layer 1030 and vacuum/medium 1040. The initial values of the parameters may be those expected for the target being measured. The measured radiation distribution 108 is then compared at 212 to the computed radiation distribution 208 to determine the difference between the two. If there is a difference, the values of one or more of the parameters of the parameterized model 206 may be varied, a new computed radiation distribution 208 calculated and compared against the measured radiation distribution 108 until there is sufficient match between the measured radiation distribution 108 and the computed radiation distribution 208. At that point, the values of the parameters of the parameterized model 206 provide a good or best match of the geometry of the actual target 30'. In an embodiment, the reconstruction of the target periodic structure parameters is achieved by minimizing a difference between the detected radiation distribution and a computed radiation distribution for a parameterized model of the target grating. The optimizer used in this reconstruction may also take into account prior knowledge on the statistical distribution of the periodic structure parameters in the lithographic process.

One or more of those determined parameters of the parameterized model (e.g., CD) may be used by the user for evaluating one or more steps of the lithographic process or other manufacturing process. Additionally or alternatively, a parameter of interest may be derived from one or more of the values of the parameterized model.

As discussed above, the geometrical and optical properties of the target are captured in a parameterized model (e.g., a model such as in FIG. 10), of which one or more parameters of interest (e.g., a CD parameter) form a subset. Using, e.g., a Maxwell solver, the values of the model parameters for the measured target are reconstructed in a computational post-processing of the recorded pupil that is called reconstruction. In an embodiment, the model may include the gap as a floating parameter to be reconstructed.

In an embodiment, to enable relatively fast calculation using, e.g., a forward model Maxwell solver, typically only one or a few features of the periodic structure of a target are modeled. Periodic boundary conditions are then used to approximate the full periodic structure. An example of a model of a single feature of a periodic structure, for use in such calculations, is shown in FIG. 10, which depicts a SIL tip 1050, the target feature and associated layers 1000, 1010, 1020, 1030, and the gap 1040 between the SIL tip 1050 and the target feature. As will be appreciated, the SIL, gap, target feature and/or layers may have different refractive index (e.g., a real or complex refractive index, refractive index tensor, etc.) as roughly represented in the FIG. 10 example by the different pattern fill.

Alternatively or additional to measurement of a parameter by reconstruction, a measured radiation distribution is useful in the measurement of asymmetry of features in product and/or resist patterns. A particular application of asymmetry measurement is for the measurement of overlay, where the target 30 comprises one set of periodic features superimposed on another. While the positions of the diffraction orders in the diffraction spectrum of the target are determined only by the periodicity of the target, asymmetry in the diffraction spectrum is indicative of asymmetry in the individual features which make up the target. Such asymmetry in the diffraction orders appears directly as asymmetry in the pupil image recorded by detector 18. This asymmetry can be measured by digital image processing in unit PU, and calibrated against known values of overlay.

As discussed above, periodic structure pitch shrink may increasingly cause parameters of the periodic structure to become correlated in the detected radiation distribution from the periodic structure. That is, for two different parameters of the periodic structures, changes in the detected radiation distribution due to a small change in these parameters of the periodic structure become increasingly similar. This can cause the performance of the metrology apparatus (e.g., the results of determining of one or more parameters of interest from analysis of the detected radiation distribution) to decrease with decreasing pitch of the periodic structure of the metrology target. In addition or alternatively, the signal-to-noise ratio may decrease with decreasing pitch and so cause the performance of the metrology apparatus (e.g., the results of determining of one or more parameters of interest from analysis of the detected radiation distribution) to decrease. Thus, the precision with which one or more dimensions and/or optical parameters of a metrology target periodic structure are reconstructed is limited by signal to noise of the detected radiation distribution and parameter cross correlation. Thus, in an embodiment, it is desirable to provide one or more measures to improve the performance of the metrology apparatus by taking one or more steps to reduce the effects of detected intensity noise (improve the signal to noise ratio) and/or counteract parameter cross correlation (improve parameter decorrelation). By reducing the effects of detected intensity noise (improving the signal to noise ratio) and/or counteracting parameter cross correlation (improving parameter decorrelation), a better results may be obtained from a metrology apparatus at future smaller device feature sizes (smaller pitches of metrology target periodic structures).

In an embodiment, the signal to noise ratio may be improved by multi-frame averaging. That is, a plurality of radiation distributions (N radiation distributions) are acquired for a particular gap size and then the pixel values of these N frames are averaged. The result is an improvement of the signal to noise ratio by the sqrt(N). This, however, may not improve parameter cross correlation in the pupil as discussed above.

In an embodiment, numerical modeling may be used to predict a measurement beam wavelength from the measurement apparatus spectral range (e.g., select a wavelength from the spectral range of 425-700 nm) that would yield a smallest parameter cross correlation or a low parameter cross correlation (e.g., 130% or less, 120% or less, 110% or less, 105% or less, 102% or less, 101% or less, of the smallest predicted parameter cross correlation).

In an embodiment, numerical modelling may be used to predict two or more measurement beam wavelengths from the measurement apparatus spectral range (e.g., select a plurality of wavelengths from the spectral range of 425-700 nm) that would yield a smallest parameter cross correlation when reconstruction is performed using data of two or more radiation distributions measured with the respective two or more measurement beam wavelengths, or a low parameter cross correlation (e.g., 130% or less, 120% or less, 110% or less, 105% or less, 102% or less, 101% or less, of the smallest predicted parameter cross correlation when reconstruction is performed using the data of the two or more radiation distributions measured with the respective two or more measurement beam wavelengths) when reconstruction is performed using the data of the two or more radiation distributions measured with the respective two or more measurement beam wavelengths. Different wavelengths can reduce, if not break, each other's parameter correlations when the set of respective radiation distributions is considered. A fast wavelength switching unit may be needed to take the measurements at the multiple wavelengths in order to keep or obtain a relatively high throughput.

In an embodiment, reconstruction precision, expressed as a variance of a set of measurements, can be improved by constraining the solver to a trusted region around a nominal preset parameter value. One such constraining technique is Bayesian regularization.

In an embodiment, parameter correlation can be reduced by acquiring more than one radiation distribution of a same target, each radiation distribution of the target obtained at a different gap size between the final optical element of the metrology apparatus and the target. That is, in an embodiment, parameter correlation can be reduced by acquiring more than one radiation distribution of a target in the back focal plane (or its conjugate) of a metrology apparatus employing a SIL 60 or other optical element in the near field of the target, each radiation distribution of the target obtained at a different gap size between the SIL 60, or other optical element in the near field of the target, of the measurement apparatus and the target. For example, the radiation distributions can be detected at, e.g., 20, 40, 60 and 80 nm gap size. The number of gap sizes can be two different gap sizes, three different gap sizes, four different gap sizes, etc. The number of gap sizes would be limited by the impact on throughput to obtain those different radiation distributions. In an embodiment, a uniform difference in gap size is applied for three or more gap sizes (e.g., 5 nm difference, 10 nm difference, 15 nm difference, 20 nm difference, 25 nm difference, or 30 nm difference) or a non-uniform difference in gap size is applied for three or more gap sizes. As discussed above, the gap sizes may be obtained by causing relative movement between the SIL 60 and the target. For example, the SIL 60 may be moved to a respective plurality of setpoint distances and then the radiation distributions are obtained when the SIL 60 is at the respective setpoint distances. Additionally or alternatively, the radiation distributions may be detected during an increasing or decreasing gap distance. For example, the SIL 60 may be moved to a setpoint distance that acts as an endpoint or starting point of a motion during at least part of which motion the radiation distributions are detected.

Once the measured radiation distributions are obtained at respective different gap heights or distances, a parameter of interest can be derived by a reconstruction similar to as described above by minimizing a difference between data of the measured radiation distributions at respective different gap heights or distances (e.g., four measured radiation distributions) and data of the corresponding calculated radiation distributions at the respective different gap heights or distances (e.g., four calculated radiation distributions). This minimization could be done by optimizing a set of floating parameters of the target periodic structure in a separate calculation unit cell corresponding to each measured radiation distribution. Each unit cell would comprise an identical set of floating parameters of the target periodic structure and a floating gap height parameter that is different for each of the unit cells. The solver will subsequently find one set of optimal parameters for the target periodic structure (including the one or more parameters of interest) and a corresponding plurality of optimal values of the reconstructed gap height for each measured radiation distribution.

It is expected that the above proposed multi-gap distance reconstruction can reduce, if not eliminate, parameter cross correlation since the measured intensity results from the multiple interference between the radiation reflected at the target periodic structure and the radiation reflected at the interface between the SIL and the environment in the gap. By measuring the intensity distribution, which is the result of this interference, at multiple gap distances, information is obtained that contains the reflected amplitude and phase depth of the periodic structure. The phase depth of the periodic structure appears to be quite sensitive to the nature of the grating. Further, the relative phase-shifts in the NA>1 region, accessed through NA>1 measurement as described herein, appears to be significantly larger than those in the NA<1 region.

In an embodiment, the plurality of radiation distributions obtained at the respective multiple gap heights may be obtained using a single nominal measurement beam wavelength. This may potentially improve throughput as the decorrelation is not tied to limitations associated with switching between various wavelengths (e.g., a fast wavelength switching unit). Rather, the throughput would be limited by the bandwidth of the control system that controls the relative movement between the SIL and the target (which may be high). But, in an embodiment, a change in gap height can be accompanied by a change in measurement beam wavelength. As mentioned above, measuring at two different wavelengths can lead to parameter decorrelation. This parameter decorrelation due to measuring at different wavelengths can be (partly) orthogonal to the parameter decorrelation due to gap height variation. So, combining obtaining radiation distributions at different gap heights and different measurement beam wavelengths may therefore lead to further parameter decorrelation without an increase of acquisition time with respect to a conventional multi-wavelength reconstruction. In an embodiment, each different gap height may be associated with a different measurement beam wavelength. In an embodiment, at least one of the different gap heights may be associated with a different measurement beam wavelength (such that there are at least two different measurement beam wavelengths among the plurality of different gap heights). In an embodiment, each different gap height is measured using each of a plurality of different measurement beam wavelengths. In an embodiment, each of a plurality of different measurement beam wavelengths may be used for measurements at a plurality of gaps, with two or more different wavelengths used for measuring at essentially identical gaps and other and/or identical wavelengths used for measuring at different gaps. Thus, not all wavelengths need to have different gaps; one gap may be used by more than one wavelength.

In an embodiment, a change in gap height can be accompanied by a change in measurement beam polarization. Measuring at two different polarizations may lead to parameter decorrelation. This parameter decorrelation due to measuring at different polarization may be (partly) orthogonal to the parameter decorrelation due to gap height variation. In an embodiment, each different gap height may be associated with a different measurement beam polarization. In an embodiment, at least one of the different gap heights may be associated with a different measurement beam polarization (such that there are at least two different measurement beam polarizations among the plurality of different gap heights). In an embodiment, each different gap height is measured using each of a plurality of different measurement beam polarizations.

There is likely an optimal number and combination of gap heights (e.g., number and/or size) to ensure optimal parameter decorrelation for a given use-case. The optimal number of different gap heights and/or the optimal values of the different gap heights at which the radiation distribution is measured, as well as with which two or more different wavelengths and/or two or more different polarizations the different gap heights are potentially combined, can be determined in the measurement apparatus recipe generation process (the process used to determine which one or more wavelengths, one or more polarizations, one or more gap heights, etc. are used to measure the metrology target). For example, for a certain use case, it can be determined that a measurement series of three gaps is optimal and that optimal height values are 21, 34 and 57 nm, respectively. In an embodiment, such a recipe is generated once for a single process step.

In an embodiment, at the time of the acquisition of the radiation distributions (e.g., just before, during, or just after detection of the radiation distributions), the gap height may be measured using a control signal (e.g., gap error signal (GES)), which additional information may be used in a modified reconstruction process using the minimization process described above for multiple gap heights. The additional information will be smeared out (time-integrated) due to its continuous acquisition, but the effect on throughput will be smaller as potentially fewer radiation distribution measurements are collected.

A change from one gap height to another gap height may require a refocusing of the optical spot onto the target. But, in an embodiment, such focusing may be implemented at least partially in parallel with the change in gap height where, for example, a dual stage (SIL stage and objective stage) control concept is employed. In such a system, the focusing control may be independent from the gap height control.

Figure 11:
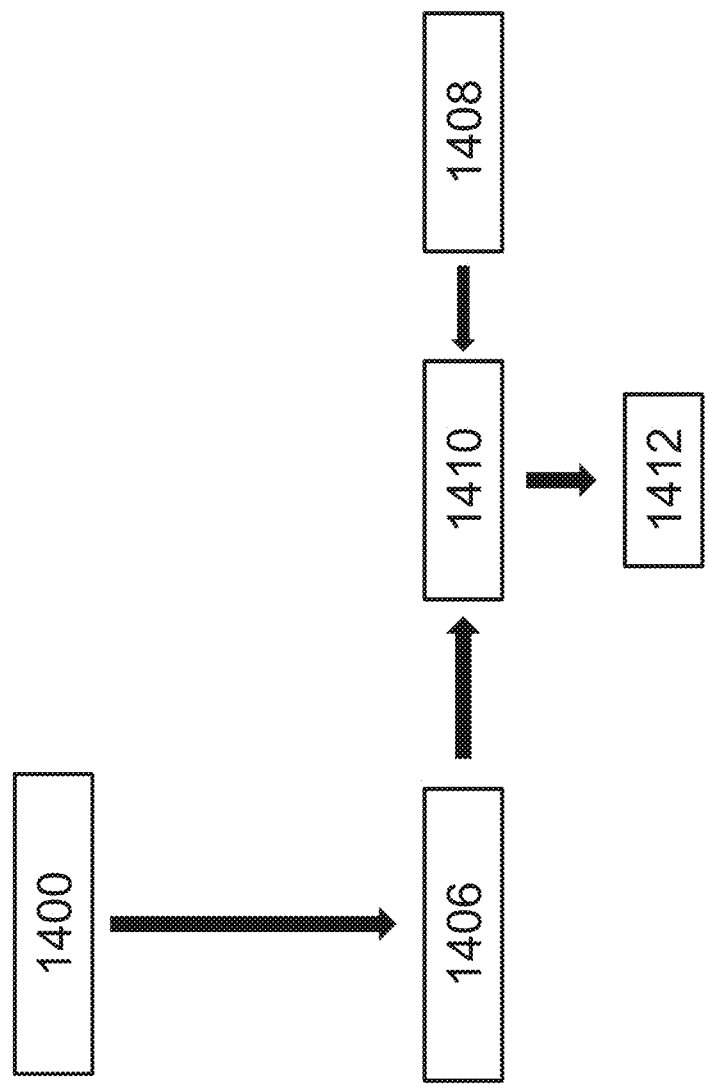
FIG. 11 schematically depicts a flow diagram of a process to derive one or more parameters of interest of a target based on a measured data obtained using a SIL.

FIG. 11 schematically depicts a flow diagram of a process of reconstruction using a model of one or more parameters of a target, wherein the target is measured using a SIL at a plurality of gap distances. At 1400, a nominal parametric model for the target structure is set up (e.g., with dimensions of one or more layers associated with the target, one or more refractive indices of one or more layers, one or more nominal gap values for the measurements, one or more measured radiation wavelengths and/or polarizations, etc.).

In an embodiment, a separate calculation unit cell corresponding to each different gap height may be used, each unit cell having a set of floating parameters of the target periodic structure. Each unit cell would comprise an identical set of floating parameters of the target periodic structure and a floating gap height parameter that is different for each of the unit cells. This is typically the case when all gaps are measured at the same wavelength. If more than one wavelength is used at two or more gaps then each unit cell should comprise an identical set of floating geometrical parameters, but the set of optical parameters will be different in the various unit cells to account for dispersion of radiation dependent on the wavelength.

The solver will subsequently find one set of optimal parameters for the target periodic structure (including the one or more parameters of interest) and a corresponding plurality of optimal values of the reconstructed gap height for each measured radiation distribution. That is, once the measured radiation distributions are obtained at respective different gap heights or distances, a parameter of interest can be derived by a reconstruction similar to as described above by minimizing a difference between data of the measured radiation distributions at respective different gap heights or distances (e.g., four measured radiation distributions) and data of the corresponding calculated radiation distributions at the respective different gap heights or distances (e.g., four calculated radiation distributions).

At 1406, an ideal pupil (radiation distribution) expected from measuring the target with a measurement beam using the SIL is calculated using the model of 1400.

At 1408, a plurality of radiation distributions is measured for the target using the SIL. Each radiation distribution is measured at a different gap height. Optionally, two or more different wavelengths and/or polarizations may be used in obtaining the plurality of radiation distributions as described above.

At 1410, data of the radiation distributions are applied to a reconstruction process to derive one or more parameters of interest 1412 of the target. For example, the process of FIG. 9 may be used at 1410. In an embodiment, a parameter of interest can be derived by a reconstruction similar to as described above by minimizing a difference between data of the measured radiation distributions at respective different gap heights or distances (e.g., four measured radiation distributions) and data of the corresponding calculated radiation distributions at the respective different gap heights or distances (e.g., four calculated radiation distributions). If two or more different wavelengths and/or polarizations are used, then the reconstruction process would be appropriately modified as discussed above, e.g. with non-identical optical parameters in each unit cell to account for dispersion.

In an embodiment, the optical element tip (e.g., SIL 60 tip) may be represented in the reconstruction model as being perfectly flat. But, it has been discovered that a variation in the surface of the optical element tip from an expected perfectly flat or curved surface thereof (hereinafter roughness) can yield errors in measurement results. Thus, in an embodiment, the optical effect of roughness can be modeled by an effective medium approximation (EMA), in which the roughness is represented in the model by one or more continuous segments having an effective refractive index (e.g., a real or complex refractive index, refractive index tensor, etc.). That is, the effective medium approximation of the optical element tip roughness is used in the modeling, e.g., reconstruction of a parameter of interest from measured radiation. An example of such an EMA is Bruggeman's EMA, in which the roughness is represented by a single layer of thickness T and effective refractive index neff. Other EMA's include Maxwell-Garnett Theory, Drude, Volume Averaging Theory, Lorentz-Lorenz, Parallel and/or Series EMA. Any EMA model is determined by a set of parameters, which will be referred to as the EMA parameters.

In an embodiment, the values of EMA parameters (e.g., the values of T and neff) may be obtained from a calibration procedure. In an embodiment, to calibrate the EMA parameters of a certain model geometry and to reduce mathematical and/or measurement complexity in arriving at the EMA parameters, a reference sample surface (fiducial) that is generally plane and with accurately known optical parameters is used. Radiation is then passed through the optical element (and its rough tip) onto the fiducial. The redirected radiation is passed to a detector, where one or more radiation distributions of such redirected radiation are measured. Then, a mathematical calculation process, such as a mathematical reconstruction process similar to as discussed herein (such as in respect of FIG. 6), may be used to derive one or more parameters of the EMA model.

The intensity differences in the pupil on which the determination of the EMA parameters relies are small (e.g., on the order or smaller than one gray-scale of the detector). So, in an embodiment, to enhance the precision/accuracy with which the EMA parameters can be reconstructed, the gap distance between the optical element and the fiducial can be varied so as to obtain measured radiation distributions at a plurality of gap heights between the optical element and the fiducial. Thus, the various techniques described herein can be extended to calibration method for determining EMA parameters (e.g., different gap heights, different wavelengths, different polarizations, etc.). As a result, the calibration method can enable a better determination of the EMA parameters and/or enable the use of a more complicated EMA model with more parameters.

Further, another EMA layer may be used in the model to represent fiducial surface roughness. Where the refractive index of the fiducial is close to that of the optical element material, cross-talk between the two sets of EMA parameters (i.e., the EMA parameters for the optical element and the EMA parameters for the fiducial) may exist. So, the various techniques described herein can be extended to a calibration method for determining EMA parameters of an EMA layer for fiducial surface roughness (e.g., different gap heights, different wavelengths, different polarizations, etc.). The use of measured radiation distributions obtained for various gap distances between the optical element and the fiducial will assist in the decorrelation of the parameters of two EMA layers to enable obtain better EMA parameters for the EMA layer for the optical element and/or for the EMA layer for the fiducial.

The described techniques can be applied with a measurement apparatus having a NA>1 (e.g., having a SIL 60), but can equally be applied with a measurement apparatus having a NA<1. In an embodiment, an optical element (e.g., a planar transparent optical element) may be positioned in close proximity to the target within the focal depth of the objective lens and the distance between the optical element and the target varied as discussed herein. In this case, the objective lens should be well corrected for focusing through such an optical element. In an embodiment, the optical element is transparent and located between a NA<1 objective and the target. In an embodiment, the optical element may have a thin partially transparent and partially reflective coating to enhance the multiple reflections between the optical element and the target.

Thus, in embodiment, there is provided a method of improving metrology precision by performing the parameter of interest determination (e.g., target reconstruction) using data of radiation distributions obtained at more than one gap distance between a target and an optical element of the metrology apparatus near the target. Using such multiple gap distances, the plurality of radiation distributions obtained at those multiple gap distances can improve metrology bias and precision.

So, in an embodiment, there is provided a target structure reconstruction based on data from more than one detected radiation distribution (e.g., angular resolved detected radiation distribution), each detected radiation distribution at a different gap distance between an optical element of a measurement apparatus and the target. In an embodiment, the optical element may be a hyper-NA SIL. In an embodiment, the optical element may be an optical element nearest the target of a measurement apparatus having a numerical aperture less than or equal to 1. In an embodiment, the optical element may be a transparent optical element located between the target and an objective having a numerical aperture of less than or equal to 1.

So, in an embodiment, there is provided a target structure reconstruction based on data from more than one radiation distribution detected during a relative motion between the target and an optical element of a measurement apparatus (e.g., during a continuously increasing or decreasing gap distance between the optical element and the target).

So, in an embodiment, there is provided a target structure reconstruction based on more than one detected radiation distribution, each detected radiation distribution at a different gap distance between an optical element of a measurement apparatus and the target and at least two of the radiation distributions measured using a respectively different measurement wavelength.

As described above, in an embodiment, there are provided various techniques to process a parameter of interest from measurement data. The techniques have particular applicability in an optical metrology or inspection apparatus such as a scatterometer, an alignment sensor (which determines alignment using one or more alignment marks), an encoder or interferometer (which enables position measurement), and/or a height or level sensor (which enables measuring of the position of a surface). But, while the embodiments disclosed herein use optical metrology as an application of the disclosed techniques, the techniques can be applied in other applications, such as used to reconstruct a structure based on radiation captured by SILs or NA<1 optical elements, or in any other applications where an object is positioned and/or maintained close to another object (e.g., in the below 400 nm range) or within the coherence length of the measurement beam for NA<1 optical elements. The techniques need not be applied exclusively, and could be applied in combination with one or more other techniques, including one or more techniques discussed in the cited documents.

While discussion herein has focused on a lithographic process, the techniques described herein may be used in or other manufacturing process (e.g., etching, resist developing, etc. processes).

Reference to the gap is not intended to imply that a medium between SIL 60 and target 30 must be, e.g., air, or even that it must be gaseous. The medium within the gap in any particular implementation may be a vacuum or partial vacuum, any gaseous or liquid medium, whose refractive index meets the requirements of the optical functions of the apparatus.

Detectors described herein may measure the intensity of radiation at a single wavelength (or narrow wavelength range), the intensity separately at multiple wavelengths or the intensity integrated over a wavelength range. Detectors described herein may separately measure the intensity of transverse magnetic- and transverse electric-polarized radiation and/or the phase difference between the transverse magnetic- and transverse electric-polarized radiation. Detectors described herein may detect polarized radiation passing via a polarizer and so provide polarization sensitive detection without, for example, necessarily measuring polarization.

The algorithms described in this document may be implemented via coding of a suitable software program to be performed by, e.g., processor system PU or its equivalent in the form of a dedicated microprocessor or the like.

Any controllers or control systems described herein may each or in combination be operable when the one or more computer programs are read by one or more computer processors located within at least one component of the lithographic apparatus or measurement apparatus. The controllers may each or in combination have any suitable configuration for receiving, processing, and sending signals. One or more processors are configured to communicate with the at least one of the controllers. For example, each controller may include one or more processors for executing the computer programs that include machine-readable instructions for the methods described above. The controllers or control systems may include a data storage medium for storing such computer programs, and/or hardware to receive such medium. So the controller(s) or control system(s) may operate according the machine readable instructions of one or more computer programs.

Although specific reference may be made in this text to the use of embodiments in the context of metrology or inspection apparatus used to inspect or measure items in association with, e.g., optical lithography and/or manufacture of ICs, it will be appreciated that the methods and apparatus described herein may be used in other applications, for example imprint lithography, the use or manufacture of integrated optical systems, the use or manufacture of guidance and detection patterns for magnetic domain memories, the use or manufacture of flat-panel displays, the use or manufacture of liquid-crystal displays (LCDs), the use or manufacture of thin film magnetic heads, etc.

The substrate referred to herein may be processed, before or after exposure/patterning, in for example a track (a tool that typically applies a layer of resist to a substrate and develops the patterned/exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed or unprocessed layers.

Although specific reference may have been made above to the use of embodiments of the invention in the context of optical lithography, it will be appreciated that the invention may be used in other applications, for example imprint lithography, and where the context allows, is not limited to optical lithography.

The terms "radiation" and "beam" used herein encompass all types of electromagnetic radiation, including ultraviolet (UV) radiation (e.g. having a wavelength of less than about 400 nm and greater than about 20 nm, or about 365, 355, 248, 193, 157 or 126 nm), extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, diffractive, magnetic, electromagnetic and/or electrostatic optical components.

While specific embodiments have been described above, it will be appreciated that the invention may be practiced otherwise than as described. For example, an embodiment may take the form of a computer program containing one or more sequences of machine-readable instructions describing a method as disclosed above, or a non-transitory data storage medium (e.g. semiconductor memory, magnetic or optical disk) having such a computer program stored therein, or a transitory medium having such a computer program therein. Further, the machine readable instruction may be embodied in two or more computer programs. The two or more computer programs may be stored on one or more different data storage media.

The descriptions above are intended to be illustrative, not limiting. Thus, it will be apparent to one skilled in the art that modifications may be made to the invention as described without departing from the scope of the claims set out below.

The invention claimed is:

1. A method comprising:
obtaining a plurality of radiation distributions of measurement radiation redirected by a same measurement target, each of the plurality of radiation distributions obtained at a different gap distance between the target and an optical element of a measurement apparatus, the optical element being the nearest optical element to the target used to provide the measurement radiation to the target; and
determining a parameter related to the target using a combination of data of the plurality of radiation distributions in conjunction with a mathematical model describing the target.

2. The method of claim 1, wherein at least two of the radiation distributions are obtained with a different respective measurement beam wavelength.

3. The method of claim 1, wherein at least two of the radiation distributions are obtained with a different respective measurement beam polarization.

4. The method of claim 1, wherein the plurality of radiation distributions is obtained at least in part during a relative motion between the target and the optical element.

5. The method of claim 1, wherein the optical element comprises a solid immersion lens.

6. The method of claim 1, wherein the radiation distributions are angular resolved detected radiation distributions.

7. The method of claim 1, wherein the parameter comprises at least one selected from: a critical dimension of a feature of the target, a radiation focus used to print the target, a radiation dose used to print the target, overlay, and/or alignment.

8. The method of claim 1, wherein obtaining the plurality of radiation distributions comprises:
illuminating, using the optical element, the target with radiation; and
measuring radiation redirected by the target using a detector.

9. The method of claim 1, wherein the target comprises a fiducial and the parameter comprises a parameter of an effective medium approximation in the model for roughness of a surface of the optical element.

10. The method of claim 1, wherein determining the parameter comprises a target reconstruction.

11. The method of claim 1, wherein determining the parameter comprises minimizing a difference between data of the radiation distributions and data corresponding to the radiation distributions at the respective different gap distances determined using the model.

12. The method of claim 1, wherein the mathematical model comprises a unit cell model representing a period of a periodic structure of the target.

13. The method of claim 12, comprising a separate unit cell model for each radiation distribution, each unit cell having an identical set of floating parameters of the target and a floating gap distance parameter that is different for each of the unit cells.

14. The method of claim 1, wherein the measurement apparatus has numerical aperture of greater than 1.

15. The method of claim 1, wherein the optical element is a transparent optical element positioned between the target and an objective having a numerical aperture of less than or equal to 1.

16. The method of claim 15, where the optical element comprises a partially transparent and partially reflective coating.

17. A method of manufacturing devices wherein a device pattern is applied to a series of substrates using a lithographic process, the method including inspecting at least a target formed as part of or beside the device pattern on at least one of the substrates, using the method of claim 1, and controlling the lithographic process for later substrates in accordance with the parameter of the method.

18. A non-transitory computer program product comprising machine-readable instructions that when execute cause a processor to at least:
obtain a plurality of radiation distributions of measurement radiation redirected by a same measurement target, each of the plurality of radiation distributions obtained at a different gap distance between the target and an optical element of a measurement apparatus, the optical element being the nearest optical element to the target used to provide the measurement radiation to the target; and
determine a parameter related to the target using a combination of data of the plurality of radiation distributions in conjunction with a mathematical model describing the target.

19. A system comprising:
an inspection apparatus configured to provide a beam on a measurement target on a substrate and to detect radiation redirected by the target to determine a parameter of a lithographic process; and
the non-transitory computer program product of claim 18.

20. The system of claim 19, further comprising a lithographic apparatus, the lithographic apparatus comprising a support structure configured to hold a patterning device to modulate a radiation beam and a projection optical system arranged to project the modulated onto a radiation-sensitive substrate.

* * * * *